US012168693B2

(12) United States Patent
Van Eenennaam et al.

(10) Patent No.: US 12,168,693 B2
(45) Date of Patent: Dec. 17, 2024

(54) COMBINING CD27 AGONISTS AND IMMUNE CHECKPOINT INHIBITION FOR IMMUNE STIMULATION

(71) Applicant: ADURO BIOTECH HOLDINGS, EUROPE B.V., Oss (NL)

(72) Inventors: Hans Van Eenennaam, Nijmegen (NL); Andrea Van Elsas, Oss (NL)

(73) Assignee: ADURO BIOTECH HOLDINGS, EUROPE B.V., Oss (NL)

(*) Notice: Subject to any disclaimer, the term of this patent is extended or adjusted under 35 U.S.C. 154(b) by 712 days.

(21) Appl. No.: 16/249,404

(22) Filed: Jan. 16, 2019

(65) Prior Publication Data
US 2019/0135933 A1 May 9, 2019

Related U.S. Application Data

(60) Division of application No. 15/007,345, filed on Jan. 27, 2016, now abandoned, which is a continuation-in-part of application No. PCT/NL2014/050543, filed on Aug. 2, 2014.

(30) Foreign Application Priority Data

Aug. 2, 2013 (NL) .................................... 2011262
Mar. 4, 2014 (NL) .................................... 2012361

(51) Int. Cl.
C07K 16/28 (2006.01)
A61K 39/395 (2006.01)
A61K 45/06 (2006.01)
A61K 39/00 (2006.01)

(52) U.S. Cl.
CPC ...... C07K 16/2878 (2013.01); A61K 39/3955 (2013.01); A61K 45/06 (2013.01); C07K 16/2803 (2013.01); C07K 16/2818 (2013.01); C07K 16/2827 (2013.01); C07K 16/2896 (2013.01); A61K 2039/507 (2013.01); C07K 2317/75 (2013.01)

(58) Field of Classification Search
None
See application file for complete search history.

(56) References Cited

U.S. PATENT DOCUMENTS

| | | | |
|---|---|---|---|
| 5,229,289 A | 7/1993 | Kjeldsen | |
| 7,728,114 B2 | 6/2010 | Mach | |
| 8,481,029 B2 | 7/2013 | Glennie | |
| 9,220,776 B2 | 12/2015 | Sharma | |
| 10,160,806 B2 * | 12/2018 | Bonvini | .................. A61P 31/12 |
| 2003/0035790 A1 | 2/2003 | Chen | |
| 2003/0091995 A1 | 5/2003 | Buechler | |
| 2008/0171014 A1 | 7/2008 | Wu | |
| 2010/0173324 A1 | 7/2010 | Mori | |
| 2011/0033449 A1 | 2/2011 | Glennie | |
| 2011/0274685 A1 | 11/2011 | Keler | |
| 2013/0336976 A1 | 12/2013 | Glennie | |
| 2014/0112942 A1 | 4/2014 | Eenennam | |
| 2015/0216870 A1 | 8/2015 | Grogan | |
| 2017/0267771 A1 | 9/2017 | Eenennam | |

FOREIGN PATENT DOCUMENTS

| | | | | |
|---|---|---|---|---|
| AU | 2013203270 | | 5/2013 | |
| EP | 2314628 | | 4/2011 | |
| WO | WO2004060319 | | 7/2004 | |
| WO | WO2008051424 | | 5/2008 | |
| WO | WO2012004367 | | 1/2012 | |
| WO | WO2010077634 | | 7/2013 | |
| WO | WO-2014008218 A1 * | 1/2014 | ............. A61K 45/06 |

OTHER PUBLICATIONS

Goding et al. (J Immunol 2013; 190:4899-4909). (Year: 2013).*
Rosenberg et al. (Clin Cancer Res; 17(13); pp. 4550-4557 and Suppl pp. 1-23. 2011 ). (Year: 2011).*
Van Eenennaam (Cancer Research 73(8 Supplement):Abstract 1246, Apr. 2013, pp. 1-2 as numbered by the examiner). (Year: 2013).*
Creelan (Cancer Control. 2014;21(1):80-89). (Year: 2014).*
Woo et al. (Cancer Res; 72(4); 917-27. ©2011 AACR). (Year: 2011).*
Vudattu et al. (The Journal of Immunology, 2014, 193: 587-596). (Year: 2014).*
Abbas, et al., "Functional diversity of helper T lymphocytes," Nature, 383:787-793 (1996).
Adams, et al., "Monoclonal antibody therapy of cancer," Nature Biotechnology, 23(9):1147-1157 (2005).
Alegre, et al., "An anti-murine CD3 monoclonal antibody with a low affinity for Fcγ receptors suppresses transplantation responses while minimizing acute toxicity and immunogenicity," The Journal of Immunology, 155(3):1544-1555 (1995).
Anonymous, "Combination of Anti-CD137 & Ipilimumab in Patients with Melanoma. Clinical Trial, Clinical Trials Search.Org," Jan. 2010, retiieved from http://clinicaltrialresearch.org/combination-of-anti-cd137-ipilimumab-in-patients-with-melanoma-nct00803374.html.
Arens, et al., "Constitutive CD27/CD70 Interaction Induces Expansion of Effector-Type T Cells and Results in IFNγ-Mediated B Cell Delpetion," Immunity, 15:801-812 (2001).

(Continued)

Primary Examiner — Zachary S Skelding
(74) Attorney, Agent, or Firm — THE MARBURY LAW GROUP, PLLC

(57) ABSTRACT

The present invention relates to treatments of conditions ameliorated by stimulation of an immune response, in particular by the stimulation of antigen-specific T-lymphocytes. Treatment of such conditions according to the invention is effected by the combination of an anti-human CD27 agonistic antibody together with a number of immune checkpoint inhibitors.

5 Claims, 7 Drawing Sheets
Specification includes a Sequence Listing.

(56) References Cited

OTHER PUBLICATIONS

Arens, et al., "Tumor Rejection Induced by CD70-mediated Quantitative and Qualitative Effects on Effector CD8+ T Sell Formation," The Journal of Experimental Medicine, 199(11):1595-1605 (2004).
Bahr, Deputy Commissioner for Patent Examination Policy in a Memorandum of Feb. 22, 2018 (2018) (2 pages).
Banner, et al., "Crystal structure of the soluble human 55 kd TNF receptor-human TNFI3 complex: implications for TNF receptor activation," Cell, 73(3):431-445 (1993).
Bigler, et al., "Definition of three epitopes of the CD2/7 molecule [P 120-55]present on activated normal lymphocytes,"T-Cell Antigens-Papers, Leukocyte Typing IV, 351-352. (1989).
Booy, et al., "Monoclonal and bispecific antibodies as novel therapeutics," Archivum Immunologiae et Therapiae Experimentalis, 54:85-101 (2006).
Brown, et al., "Tolerance of single, but not multiple, amino acid replacements in antibody VH CDR 2: a means of minimizing B cell wastage from somatic hypermutation?," The Journal of Immunology, 156(9):3285-3291 (1996).
Camerini, et al., "The T cell activation antigen CD27 is a member of the nerve growth factor/tumor necrosis factor receptor gene family," The Journal of Immunology, 147(9):3165-3169 (1991).
Capece, et al., "Targeting Costimulatory Molecules to Improve Antitumor Immunity," Journal of Biomedicine and Biotechnology, 179(11):7365-17 (2012).
Cormary, et al., "Induction of T-cell antitumor immunity and protection against tumor growth by secretion of soluble human CD70 molecules," Cancer Gene Therapy, 11:497-507 (2004).
Couderc, et al., "Enhancement of antitumor immunity by expression of CD70 (CD27 ligand) or CD154 (CD40 ligand) costimulatory molecules in tumor cells," Cancer Gene Therapy, 5(3):163-175 (1998).
Cragg, et al., "Signaling antibodies in cancer therapy," Current Opinion in Immunology, 11(5):541-547 (1999)
Croft, "Co-Stimulatory Members of the TNFR Family: Keys to Effective T-Cell Immunity?," Nature Reviews Immunology, 3(8):609-620 (2003).
Curran, et al., "Combination CTLA-4 Blockade and 4-1BB Activation Enhances Tumor Rejection by Increasing T-Cell Infiltration, Proliferation and Cytokine Production," PLoS One, 6(4):e19499 (2011).
Damschroder, et al., "Analysis of human and primate CD2 molecules by protein sequence and epitope mapping with anti-human CD2 antibodies," Molecular Immunology, 41(10):985-1000 (2004).
Dong, et al., "CD148 and CD27 are Expressed in B Cell Lymphomas Derived from both Memory and Naive B Cells," Leukemia and Lymphoma, 43(9):1855-1858 (2002).
Engelmann, et al., "Antibodies to a soluble form of a tumor necrosis factor (TNF) receptor have TNF-like activity," The Journal of Biological Chemistry, 265(24):14497-14504 (1990).
French, et al., "CD40 antibody evokes a cytotoxic T-cell response that eradicates lymphoma and bypasses T-cell help," Nature Medicine, 5(5):548-553 (1999).
French, et al., "Eradication of lymphoma by CD8 T cells following anti-CD40 monoclonal antibody therapy is critically dependent on CD27 costimulation," Blood, 109:4810-4815 (2007).
Gershoni, et al., "Epitope Mapping—The First Step in Developing Epitope-Based Vaccines," BioDrugs, 21(3):146-156 (2007).
Giuntoli, et al., "Direct Costimulation of Tumor-reactive CTL by Helper T Cells Potentiate Their Proliferation, Survival, and Effector Function," Clinical Cancer Research, 8:922-931 (2002).
Glennie, et al., "Clinical trials of antibody therapy," Immunology Today, 21(8):403-410 (2000).
Goodwin, et al., "Molecular and Biological Characteiization of a Ligand for CD27 Defines a New Family of cytokines with Homology to Tumor Necrosis Faetor," Cell, 73:447-456 (1993).
Gravestein, et al., "CD27 Cooperates with the Pre-T Cell Receptor in the Regulation of Murine T Cell Development," The Journal of Experimental Medicine, 184(2):675-685 (1996).
Gravestein, et al., "Novel mAbs reveal potent co-stimulatory activity of murine CD27," International Immunology, 7(4):551-557 (1996).
Gravestein, et al., "The TNF receptor family member CD27 signals to Jun N-terminal kinase via Traf-2," European Journal of Immunology, 28(7):2208-2216 (1998).
Gray, et al., "Optimising anti-tumour CD8 T-cell responses using combinations of immunomodulato antibodies," European Journal of Immunology, 38(9):2499-2511 (2008).
Gray, et al., "Therapeutic potential of immunostimulatory monoclonal antibodies," Clinical Science, 111(2):93-106 (2006).
Gruss, et al., "Tumor necrosis factor ligand superfamily: involvement in the pathology of malignant lymphomas," Blood, 85(12):3378-3404 (1995).
Guo, et al, Combined TIM-3 blockade and CD137 activation affords the long-term protection in a murine model of ovarian cancer, Journal of Translational Medicine, 11(1):215 (2013).
Guo, et al., "PD-1 Blockade and OX40 Triggering Synergistieally Protects against Tumor Growth in a Murine Model of Ovarian Cancer," PLOS One, 9(2):e89350 (2014).
Harlow et al., "Antibody Response," A Laboratory Manual, Cold Spring Harbor Laboratory, pp. 37-47 (1988).
Haswell, et al., "Analysis of the oligomerie requirement for signaling by CD40 using soluble multimeric forms of its ligand, CD154," European Journal of Immunology, 31(10):3094-3100 (2001).
He et al., "Combination therapies augment the anti-tumor activity of agonist anti-CD27 transgenic mouse models IFNg + CD4 T cells," Nov. 2013, retrieved from http://www.celldex.coom/doc/SITCPoster2013finalversion_Preclinical-Combination-Therapies.pdf.
He et al., "Combination therapies augment the anti-tumor activity of agonist CD27 mAb in human CD27 transgenic mouse models," Journal for Immunotherapy of Cancer, 1(Suppl.1):76 (2013).
He, et al., "Abstract 5343: Development of novel anti-CD27 human antibodies with therapeutic potential," Cancer Research 70:5343 (2010).
He, et al., "Development of Novel Anti-CD27 Human Antibodies with Therapeutic Potential,"Celldex Therapeuties Inc. (Apr. 21, 2010) (1 page).
Hendriks, "Contributions of CD27 and relatives to the specific immune response," PhD Thesis, Chapter 2 (2004).
Hendriks, et al., "CD27 is required for generation and long-term maintenance of T cell immunity," Nature Immunology, 1(5):433-440 (2000).
Hendriks, et al., "CD27 Promotes Survival of Activated T Cells and Complements CD28 in Generation and Establishment of the Effector T Cell Pool," The Journal of Experimental Medicine, 198(9):1369-1380 (2003).
Hurwitz, et al., "Costimulatory wars: the tumor menace," Current Opinion in Immunology, 12(5):589-596 (2000).
Jokiranta, et al., "Biotinylation of monoclonal antibodies prevents their ability to activate the classical pathway of complement," The Journal of Immunology, 151(4):2124-2131 (1993).
Kedl, et al., "CD40 stimulation accelerates deletion of tumor-specific CD8+ T cells in the absence of tumor-antigen vaccination," PNAS, 98(19):10811-10816 (2001).
Keller, et al., "Expression of Costimulatog Ligand CD70 on Steady-State Dendritic Cells Breaks CD8+ T Cell Tolerance and Permits Effective Immunity" Immunity, 29(6):934-946 (2008).
Kelly, et al., "Induction of tumor-specific T cell memory by NK cell-mediated tumor rejection," Nature Immunology, 3(1):83-90 (2002).
Kobata, et al., "CD27 is a signal-transducing molecule involved in CD45RA+ naive T cell costimulation," The Journal pf Immunology, 153:5422-5432 (1994).
Leach, et al., "Enhancement of Antitumor Immunity by CTLA-4 Blockade," Science, 271(5256):1734-1736 (1996).
Lee et al., "Novel antibodies targeting immune regulatory checkpoints for cancer therapy," British Journal of Clinical Pharmacology, 76(2):233-247 (2013).
Lorenz, et al., "Anti-Tumor Immunity Elicited by a Recombinant Vaccinia Virus Expressing CD70 (CD27L)," Human Gene Therapy, 10:1095-1103 (1999).

(56) References Cited

OTHER PUBLICATIONS

Lu, et al., "Combined PD-1 blockade and GITR triggering induce a potent antitumor immunity in murine cancer models and synergizes with chemotherapeutic drugs," Journal of Translational Medicine, 12:36 (2014).
Manocha et al., "Blocking CD27-CD70 costimulatory pathway suppresses experimental colitis," Journal of Immunology, 183(1):270-276 (2009).
Matter, et al., "Elimination of chronic viral infection by blocking CD27 signaling," The Journal of Experimental Medicine, 203(9):2145-2155 (2006).
Melero, et al., "Agonist Antibodies to TNFR Molecules That Costimulate T and N Cells," Clinical Cancer Research, 19(5):1044-1053 (2013).
Mellman, et al., "Cancer immunotherapy comes of age" Nature, 480(7378):480-489 (2011).
Nakajima et al., "Involvement of CD70-CD27 interactions in the induction of experimental autoimmune encephalomyelitis," Journal of Neuroimmunology, 109(2):188-196 (2000).
Nieland, et al., "CD40 and CD70 Co-Stimulate a Potent In Vivo Antitumor T Cell Response," Journal of Immunotherapy, 21(3):225-236 (1998).
Nolte, et al., "The mice of the CD27-CD70 costimulatory axis: you can't have it all," The Journal of Experimental Medicine, 203(11):2405-2408 (2006).
Oelke et al., "Overexpression of CD70 and overstimulation of IgG synthesis by lupus T cells and T cells treated with DNA methylation inhibitors," Arthritis & Rheumatism, 50(6):1850-1860 (2004).
Oflazoglu et al., "Blocking of CD27-CD70 pathway by anti-CD70 antibody ameliorates joint disease in murine collagen-induced arthritis," Journal of Immunology, 183(6)3770-3777 (2009).
Pardoll, "Spinning Molecular Immunology into Successful Immunotherapy," Nature Reviews Immunology, 2:227-238 (2002).
Pardoll, "The blockade of immune checkpoints in cancer immunotherapy" Nature Reviews Cancer, (4):252-264 (2012).
Park, et al., "Monoclonal Antibody Therapy," Advances in Protein Chemistry, 56:369-421 (2001).
Parlevliet, et al., "In Vivo Effects of IgA and IgGZa Anti-CD3 Isotype Switch Variants," Journal of Clinical investigation, 93(6):2519-2525 (1994).
Penichet, et al., "Design and Engineering Human Forms of Monoclonal Antibodies," Drug Development Research, 61:121-136 (2004).
Prasad, et al., "CD27, a member of the tumor necrosis factor receptor family, induces apoptosis and binds to Siva, a proapoptotic protein," PNAS, 94(12):6346-6351 (1997).
Raju, "Glycosylation Variations with Expression Systems and Their Impact on Biological Activity of Therapeutic Immunoglobulins," BioProcess International, pp. 44-53 (2003).
Roberts, et al., "Control of established melanoma by CD27 stimuiation is associated with enhanced effector function and persistence, and reduced PD-1 expression, of tumor infiltrating CD8+ T cells," Journal of Immunotherapy, 33(8):769-779 (2010).
Roberts, et al., "Control of established melanoma by CD27 stimulation is associated with enhanced effector 'unction and persistence, and reduced PD-1 expression of tumor infiltrating CD8+ T cells" Journal of Immunotherapy, 33(8):769-779 (2010).
Rowley, et al., "Stimulation by Soluble CD70 Promotes Strong Primary and Secondary CD8+ Cytotoxic T Cell Responses In Vivo," The Journal of Immunology, 172(10):6039-6046 (2004).
Rudikoff, et al., "Single amino acid substitution altering antigen-binding specificity," PNAS, 79(6):1979-1983 (1982).
Sakanishi, et al., "Anti-tumor effects of depleting and non-depleting anti-CD27 monoclonal antibodies in immune-competent mice," Biochemical and Biophysical Research Communications, 393(4):829-835 (2010).

Sakuishi, et al., "Targeting Tim-3 and PD-1 path s to reverse T cell exhaustion and restore anti-tumor irnmunity," Nature Reviews Immunology, 6(10):2187-2194 (2010).
Santa Cruz Biotechnology, "CD27 (M-T271): sc-19653" (1 page).
Schwabe, et al., "Modulation of Soluble CD40 Ligand Bioactivity with Anti-CD40 Antibodies," Hybridoma, 16(3):217-225 (1997).
Simeone, et al., "Immunomodulating antibodies in the treatment of metastatic melanoma: The experience with anti-CTLA-4, anti-CD137 and anti-PD1," Journal of Immunotoxicology, 9(3):246 (2012).
Sino Biologics, "Immune Checkpoint Proteins," www.sinobiological.com/immune-checkpoint-proteins-elite-html (downloaded Nov. 8, 2018) (5 pages).
Takeda, et al., "CD27-Mediated Activation of Murine NK Cells" The Journal of Immunology, 164:1741-1745 (2000).
Tao, et al., "Role of Carbohydrate in the Structure and Effector Functions Mediated by the Human IgG Constant Region," The Journal of Immunology, 143(8):2595-2601 (1989).
Taraban, et al., "Cutting Edge: A Critical Role for CD70 in CD8 T Cell Priming by CD40-Licensed APCs," The Journal of Immunology, 173:6542-6546 (2004).
Thomas, et al., "Anti-tumor Activity of a Fully Human anti-CD27 Monoclonal Antibody in a Transgenic Mouse Model," American Association for Cancer Research 102nd Annual Meeting, Apr. 2011.
Thomas, et al., "Targeting human CD27 with an agonist antibody stimulates T-cell activation and antitumor immunity," Oncoimmunology, 3(1):e27255 (2014).
Tutt, et al., "T Cell Immunity to Lymphoma Following Treatment with Anti-CD40 Monoclonal Antibody," The Journal of Immunology, 168:2720-2728 (2002).
Vajdos, et al., "Comprehensive Functional Maps of the Antigen-binding Site of an Anti-ErbB2 Antibody Obtained with Shotgun Scanning Mutagenesis," Journal of Molecular Biology, 320(2):415-428 (2002).
Van Lier, et al., "Tissue Distribution and Biochemical and Functional Properties of Tp55 (CD27), A Novel T Cell Differentiation Antigen," The Journal of Immunology, 139(5):1589-1596 (1987).
Van Mierlo, et al., "CD40 stimulation leads to effective therapy of CD40-tumors through induction of strong systemic cytotoxic T lymphocyte immunity," PNAS, 99(8):5561-5566 (2002).
Vitale, et al., "Development of a Human Monoclonal Antibody for Potential Therapy of CD27-Expressing Lymphoma and Leukemia," Clinical Cancer Research, 18(14):3812-3821 (2012).
Watts, "TNF/TNFR Family Members in Costimulation of T Cell Responses," Annual Review of Immunology, 23:23-68 (2005).
Wei, et al., "Combinatorial PD-1 blockade and CD137 activation has therapeutic efficacy in murine cancer models and synergizes with cisplatin, " PLOS One, 8(12):e84927 (2013).
Wesolowski, et al., "Single domain antibodies: promising experimental and therapeutic tools in infection and immunity," Medical Microbiology and Immunology, 198:157-174 (2009).
Wieland, et al., "CD27 contributes to the early systemic immune response to Mycobacterium tuberculosis infection but does not affect outcome," International Immunology, 18(11):1531-1539 (2006).
Woo, et al., "Immune inhibitory molecules LAG-3 and PD-1 synergistically regulate T-cell function to promote tumoral immune escape," Cancer Research, 72(4):917-927 (2011).
Xu, et al., "Diversity in the CDR3 Region of VH is Sufficient for Most Antibody Specificities," Immunity, 13:37-45 (2000).
Xu, et al., "FcyRs Modulate Cytotoxicity of Anti-Fas Antibodies: Implications for Agonistic Antibody-Based Therapeutics," The Journal of Immunology, 171(2):562-568 (2003).
Zuo, "Regulatory T cells, tumour immunity and immunotherapy," Nature Reviews Immunology, 6(4):295-307 (2006).

\* cited by examiner

COMBINING CD27 AGONISTS AND IMMUNE CHECKPOINT INHIBITION FOR IMMUNE STIMULATION

RELATED APPLICATIONS AND INCORPORATION BY REFERENCE

This application is a divisional of U.S. patent Application Ser. No. 15/007,345, filed Jan. 27, 2016, (pending), which is a continuation-in-part application of PCT International Patent Application No. PCT/NL2014/050543, filed Aug. 2, 2014, which published as PCT Publication No. WO 2015/016718, Feb. 5, 2015, which claims benefit of Netherlands Patent Application Nos. NL 2011262, filed Aug. 2, 2013, and NL 2012361, filed Mar. 4, 2014.

The foregoing applications are incorporated herein by reference in their entireties.

SEQUENCE LISTING

The instant application contains a Sequence Listing which has been submitted electronically in ASCII format is hereby incorporated by reference in its entirety. Said ASCII copy, created on Jan. 16, 2019, is named 000145-0002-302-SL.txt and is 25,050 bytes in size.

FIELD OF THE INVENTION

The present invention relates to the field of human and veterinary medicine, including medical/veterinary diagnosis and medical/veterinary research. More specifically the present invention relates to treatments of conditions ameliorated by stimulation of an immune response, in particular by the stimulation of antigen-specific T-lymphocytes. The various aspects of the present invention are suitable for treatment of any condition known or expected to be ameliorated by stimulation of CD27+ immune cells or by inhibition of one or more immune checkpoint protein(s). Conditions suitably treated by the invention are those ameliorated by immune stimulation, such as infectious diseases and cancers, by using a combination of a CD27 agonist and one or more immune checkpoint blocking agents.

BACKGROUND

CD27, a TNF receptor family member was identified as a membrane molecule on human T cells (van Lier et al., 1987, J Immunol 139:1589-96). According to current evidence, CD27 has a single ligand, CD70, which is also a TNF family member (Goodwin et al., 1993, Cell 73:447-56).

CD27 is exclusively expressed by hematopoietic cells, in particular those of the lymphocyte lineage, i.e. T-, B- and NK cells. CD27 was originally defined as a human T-cell co-stimulatory molecule that increments the proliferative response to TCR stimulation (van Lier et al., 1987, J Immunol 139:1589-96). Presence of CD70, the ligand of CD27, dictates the timing and persistence of CD27-mediated co-stimulation.

Transgenic expression of CD70 in immature dendritic cells sufficed to convert immunological tolerance to virus or tumors into $CD8^+$ T cell responsiveness. Likewise, agonistic soluble CD70 promoted the CD8 T cell response upon such peptide immunization (Rowley et al., 2004, J Immunol 172:6039-6046) and in CD70 transgenic mice, $CD4^+$ and $CD8^+$ effector cell formation in response to TCR stimulation was greatly facilitated (Arens et al. 2001, Immunity 15:801-12; Tesselaar et al., 2003, Nat Immunol 4:49-54; Keller et al. 2008, Immunity 29: 334-346). In mouse lymphoma models, tumor rejection was improved upon CD70 transgenesis or injection of an anti-mouse CD27 antibody (Arens et al., 2003, J Exp Med 199:1595-1605; French et al., 2007, Blood 109: 4810-15; Sakanishi and Yagita, 2010, Biochem. Biophys. Res. Comm. 393: 829-835; WO 2008/051424; WO 2012/004367).

In WO2012/004367 the first anti-human agonistic antibody (designated hCD27.15) was described that does not require crosslinking to activate CD27-mediated co-stimulation of the immune response. In addition, an anti-human CD27 antibody, designated 1F5 was disclosed that activates CD27 upon crosslinking (WO2011/130434 and Vitale et al., Clin. Cancer Res, 2012, 18(14): 3812-3821).

Recently, the first clinical successes of agents that modulate cancer immunity have validated cancer immunotherapy as a novel path to obtain durable and long-lasting clinical responses in cancer patients (Mellman et al., Nature, 2011, 480:480-489). The first such agent, ipilimumab (Yervoy, BMS), that obtained marketing approval for treatment of metastatic melanoma is an antibody blocking the CTLA4 receptor, an immune checkpoint protein. Further immune checkpoint inhibitors under development are antibodies that block the interaction between the PD-1 receptor and its ligands PD-L1 and PD-L2 (Mullard, Nat. Rev. Drug Disc., 2013, 12:489-492). Several antibodies targeting the PD-1 pathway are currently in clinical development for treatment of melanoma, renal cell cancer, non-small cell lung cancer, diffuse large B cell lymphoma and other tumors. Although these agents have not yet been filed for marketing approval, impressive results have been obtained in early clinical studies, for example with Lambrolizumab (anti-PD1) in melanoma (Hamid et al., 2013, New. Eng. J. Med. 369:134-44).

The current state of the art does not suggest that agonists of the CD27 receptor would be rationally combined with immune checkpoint inhibitors, such as anti-PD1, anti-PDL1 or anti-CTLA4 antibodies to improve cancer immunity. In fact, available data suggest that CD27 acts, at least in part via overruling PD-1 and CTLA-4 signals or via downregulation of these immune checkpoints. First, in a T-cell tolerance model based on LCMV-derived epitopes that was demonstrated to be highly dependent on PD-1 and CTLA4 receptors the forced expression of CD70 ligand was sufficient to turn T cell tolerance into activation of T-cell immunity. Apparently these data strongly suggest that CD27 activation overrules tolerance mediated via PD-1 and CTLA4 (Keller et al., Immunity, 2008, 29:934-946. In a second model, activation of CD27 using a rat anti-mouse CD27 agonistic antibody was demonstrated to support the maintenance of $CD8^+$ T-cells, to reduce the frequency of FoxP3-expressing $CD4^+$ T-cells within tumors and to potentiate the ability of $NK1.1^+$ and $CD8^+$ tumor infiltrating cells to secrete IFN-γ in coculture with tumor cells. This enhanced function correlated with decreased levels of PD-1 expression on $CD8^+$ T-cells (Roberts et al., J Immunother., 2010, 33: 769-79).

Citation or identification of any document in this application is not an admission that such document is available as prior art to the present invention.

SUMMARY OF THE INVENTION

The current state of the art thus is, that stimulation of CD27 overrules PD-1 and CTLA-4 mediated immune tolerance and that activation using anti-CD27 antibodies results in down-regulation of these immune checkpoint receptors.

Therefore, according to the state of the art the combination of an agent that activates the CD27 receptor together with one or more immune checkpoint inhibitors would result in either efficacy that is equal or similar to CD27 activation or immune checkpoint inhibition alone.

The inventors of the present invention however have surprisingly found that the combination of a CD27 agonistic antibody together with an immune checkpoint inhibitor does have additional effects on T-cell stimulation in comparison to a CD27 agonistic antibody or an immune checkpoint inhibitor alone. In particular, the additional effects of the combination of a CD27 agonistic antibody together with an immune checkpoint inhibitor has been tested in established assays that have been clinically validated to predict anti-cancer immune responses. In these assays immune checkpoint inhibitory antibodies were demonstrated to induce elevated levels of the T-cell cytokine IL-2 upon stimulation with *Staphylococcus* Enterotoxin B in either human peripheral blood mononuclear cells or whole human blood (Dulos et al., *J. Immunother*, 2012, 35: 169-78). The clinical validation and the predictive value of this assay was subsequently established in Phase I/II clinical studies (Patnaik et al., ASCO, Chicago, 2012; Ribas et al., PEGS Summit, Boston, 2013; Hamid et al., *N. Eng. J. Med.*, 2013, 369: 134-144).

The present invention is thus based on the surprising discovery that the combination of an anti-human CD27 agonistic antibody together with an immune checkpoint inhibitor results in immune stimulation to an unexpected level. In view of the so far known relation between CD27 and immune checkpoint inhibitors the higher level of immune stimulation resulting from the combination is surprising. In view of its surprising discovery the present invention relates to treatments of conditions ameliorated by stimulation or enhancement of the immune response, in particular the treatments of conditions that result in the stimulation or enhancement of antigen-specific T-lymphocytes, such as cancer and infectious disease. More specifically, the present invention is aimed at treatment of any condition known or expected to be ameliorated by stimulation of CD27+ immune cells or by inhibition of one or more immune checkpoint protein(s). Treatment of these conditions may be further improved by using a combination of a CD27 agonist and one or more immune checkpoint blocking agents.

According to a first aspect the invention relates to an anti-human CD27 agonistic antibody, such as hCD27.15 or 1F5, or an antibody derived therefrom, for use in the treatment of a condition ameliorated by stimulation of an immune response, in particular the treatment of a condition ameliorated by stimulation of antigen-specific T-lymphocytes wherein in said treatment a number of immune checkpoint protein inhibitors is administered. By this co-administration of the anti-human CD27 agonistic antibody with a number of immune checkpoint protein inhibitors, surprising effects are obtained.

According to a further aspect the invention relates to an immune checkpoint protein inhibitor for use in the treatment of a condition ameliorated by stimulation of an immune response, in particular the treatment of a condition ameliorated by stimulation of antigen-specific T-lymphocytes, wherein in said treatment an anti-human CD27 agonistic antibody, such as hCD27.15 or 1F5, or an antibody derived therefrom, is administered. By this co-administration of the immune checkpoint protein inhibitor with an anti-human CD27 agonistic antibody, surprising effects are obtained.

Yet a further aspect of the invention relates to a combination of an anti-human CD27 agonistic antibody, such as hCD27.15 or 1F5, or an antibody derived therefrom, together with a number of immune checkpoint protein inhibitors for use in the treatment of a condition ameliorated by stimulation of an immune response, in particular the treatment of a condition ameliorated by stimulation of antigen-specific T-lymphocytes.

Still a further aspect of the invention relates to a method for treating a condition ameliorated by stimulation of an immune response, in particular the treatment of a condition ameliorated by stimulation of antigen-specific T-lymphocytes, said method comprising administering an anti-human CD27 agonistic antibody, such as hCD27.15 or 1F5, or an antibody derived therefrom, in combination with a number of immune checkpoint inhibitors.

An anti-human CD27 antibody of the invention may be selected from hCD27.15 or analogues thereof, in particular analogues which may comprise the CDRs of hCD27.15, analogues (cross-)blocking the binding of hCD27.15 to human CD27, analogues binding to the same epitope of hCD27.15 or humanized analogues of hCD27.15.

In another embodiment, the anti-human CD27 antibody is administered in combination with an anti-PD1 antibody. In one embodiment, the anti-human CD27 antibody is administered in combination with nivolumab. In another embodiment, the anti-human CD27 antibody is administered in combination with pembrolizumab. In another embodiment, the anti-human CD27 antibody is administered in combination with an anti-CTLA4 antibody. In another embodiment, the anti-human CD27 antibody is administered in combination with an anti-LAG3 antibody. In another embodiment, the anti-human CD27 antibody is administered in combination with an anti-LAG3 antibody which may comprise the heavy chain amino acid sequence of SEQ ID NO: 23 and the light chain amino acid sequence of SEQ ID NO: 24.

As the skilled person will know the published sequences for the heavy and light chain of nivolumab and pembrolizumab are as presented in SEQ ID NO: 21, 22, 19 and 20 respectively.

TABLE 1

Sequence Listing

| SEQ ID NO: | Description |
| --- | --- |
| 1 | hCD27.15 heavy chain CDR1 (AA) |
| 2 | hCD27.15 heavy chain CDR2 (AA) |
| 3 | hCD27.15 heavy chain CDR3(AA) |
| 4 | hCD27.15 light chain CDR1 (AA) |
| 5 | hCD27.15 light chain CDR2 (AA) |
| 6 | hCD27.15 light chain CDR3 (AA) |
| 7 | hCD27.15 heay chain variable region (DNA) |
| 8 | hCD27.15 heavy chain variable region (AA) |
| 9 | hCD27.15 light chain variable region (DNA) |
| 10 | hCD27.15 light chain variable region (AA) |
| 11 | 1F5 heavy chain CDR1 (AA) |
| 12 | 1F5 heavy chain CDR2 (AA) |
| 13 | 1F5 heavy chain CDR3 (AA) |
| 14 | 1F5 light chain CDR1 (AA) |
| 15 | 1F5 light chain CDR2 (AA) |
| 16 | 1F5 light chain CDR3 (AA) |
| 17 | 1F5 heavy chain variable region (AA) |
| 18 | IF5 light chain variable region (AA) |
| 19 | Pembrolizumab heavy chain (AA) |
| 20 | Pembrolizmab light chain (AA) |
| 21 | Nivolumab heavy chain (AA) |
| 22 | Nivolumab light chain (AA) |
| 23 | Anti-human LAG3 mature heavy chain (AA) |
| 24 | Anti-human LAG3 mature light chain (AA) |

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

CD27 agonistic antibodies in combination with immune checkpoint blockers unexpectedly enhance SEB induced T-cell activation in human PBMCs in comparison to CD27 agonistic antibodies and immune checkpoint inhibitors alone. FIG. 1A. CD27 agonistic antibodies in combination with anti-PD1 antibodies enhance SEB induced T-cell activation in human PBMCs. Equal amounts of the indicated antibodies were added, with a final concentration as indicated on the X-axis. Human IgG4 was used as an isotype-matched control. FIG. 1B. CD27 agonistic antibodies in combination with anti-PDL1 antibodies enhance SEB induced T-cell activation in human PBMCs. Equal amounts of the indicated antibodies were added, with a final concentration as indicated on the X-axis. Human IgG4 and/or mouse IgG1 were used as isotype-matched controls.

CD27 agonistic antibodies in combination with immune checkpoint blockers unexpectedly enhance SEB induced T-cell activation in human whole blood in comparison to CD27 agonistic antibodies and immune checkpoint inhibitors alone. FIG. 2A. CD27 agonistic antibodies in combination with anti-PD1 antibodies enhance SEB induced T-cell activation in human whole blood. Equal amounts of the indicated antibodies were added, with a final concentration as indicated on the X-axis. Human IgG4 was used as isotype-matched control. FIG. 2B. CD27 agonistic antibodies in combination with anti-PDL1 antibodies enhance SEB induced T-cell activation in human whole blood. Equal amounts of the indicated antibodies were added, with a final concentration as indicated on the X-axis. Human IgG4 and/or mouse IgG1 were used as isotype-matched controls. FIG. 2C. CD27 agonistic antibodies in combination with anti-CTLA-4 antibodies enhance SEB induced T-cell activation in human whole blood. Equal amounts of the indicated antibodies were added, with a final concentration as indicated on the X-axis. Human IgG4 and/or mouse IgG2A were used as isotype-matched controls.

CD27 agonistic antibodies in combination with immune checkpoint blockers enhance SEB induced T-cell activation in human whole blood in comparison to CD27 agonistic antibodies and immune checkpoint inhibitors alone. FIGS. 3A-3D present data for the effect of a hCD27.15 analogue in combination with anti-LAG3 (left panel) and anti-PD1 (right panel). Combination of the antibodies enhances SEB induced T-cell activation in human whole blood of different donors.

DETAILED DESCRIPTION OF THE INVENTION

Figure 1A:
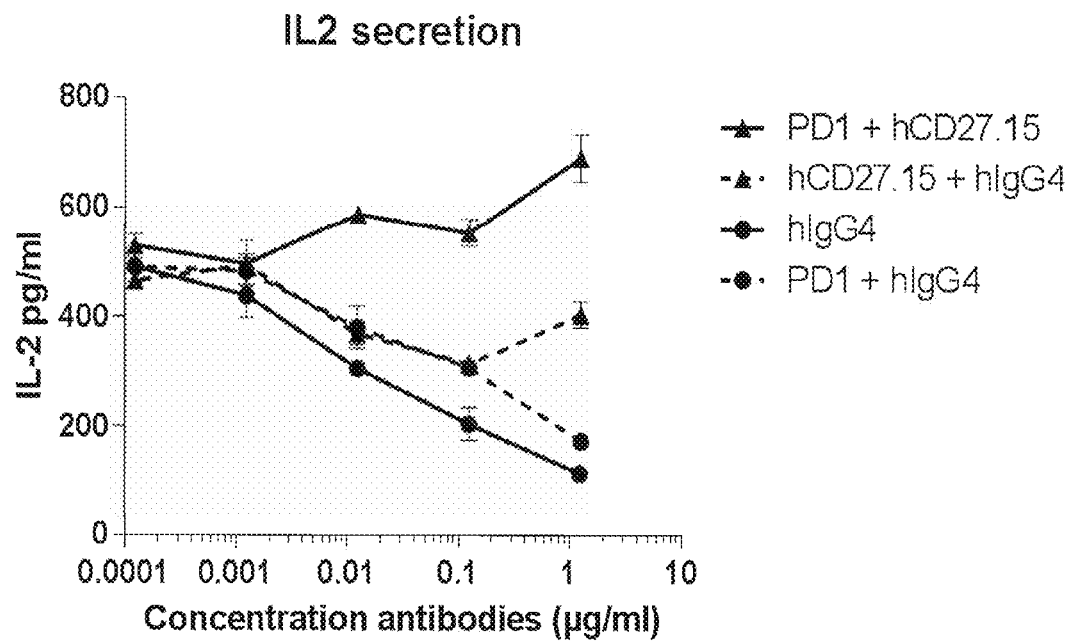
FIGS. 1A-B.

In a first aspect the invention relates to an anti-human CD27 agonistic antibody for use in the treatment of a condition ameliorated by stimulation of an immune response, in particular the treatment of a condition ameliorated by stimulation of antigen-specific T-lymphocytes, wherein in said treatment a number of immune checkpoint protein inhibitors is administered.

Anti-human CD27 agonistic antibodies should be construed as meaning an antibody demonstrating activation of the CD27 receptor on CD27$^+$ immune cells. Agonistic properties of anti-human CD27 antibodies can be assayed by CD27 receptor activation using for example the NF-κB luciferase reporter assay as described in WO2012004367. Activation of CD27 receptor using activating anti-human CD27 antibodies has been shown to induce activation, proliferation and/or survival of human CD27 immune cells. By displaying its CD27 receptor-stimulating effect the CD27 agonist is capable of inducing and/or enhancing an immune response (e.g. an antigen-specific T-cell mediated immune response). An anti-human CD27 antibody used in the present invention may exert its agonistic activity when in soluble form. Alternatively an anti-human CD27 antibody used in the present invention may exert its agonistic activity when cross-linked. For cross-linking the anti-human CD27 antibody may be adapted in respect of its Fc function. The use of anti-human CD27 antibodies exerting agonistic activity when in soluble form is preferred.

Anti-human CD27 agonistic antibodies are known in the art. For example hCD27.15 is disclosed in WO2012/004367 and 1F5 is disclosed in WO2011/130434 and Vitale et al., *Clin. Cancer Res*, 2012, 18(14): 3812-3821. The use of 1F5 or hCD27.15 or an antibody derived from one of these known antibodies is preferred. The use of hCD27.15 or an antibody analogue therefrom is most preferred in view of its beneficial binding properties and its ability to display good agonistic activity when in soluble form (without any further cross-linking). Within the present invention an antibody derived from a certain antibody may be considered an analogue. The skilled person will understand that for a proper functioning of an antibody analogue within the context of this invention, a derived antibody (or antibody analogue), according to certain embodiments, may comprise antigen binding regions of its originating antibody or will at least bind to the same epitope. Antibody analogues may (cross-)block binding of the anti-CD27 antibody, for example hCD27.15 or 1F5, to human CD27. Antibody analogues in particular may comprise antibody fragments, antibodies having modified effector function, chimeric antibodies and humanized antibodies as defined below. The antibody analogue according to the invention maintains CD27 agonistic functionality.

The heavy chain CDR1, CDR2 and CDR3 amino acid sequences and light chain CDR1, CDR2 and CDR3 amino acid sequences of hCD27.15, identifying the antigen binding region of this antibody, are already disclosed in WO2012/004367. These sequences have also been presented in SEQ ID NO: 1-6 of the sequence listing of this description, together with the amino acid sequences of the heavy chain variable region and the light chain variable region (SEQ ID NO: 8 and 10 respectively). Antibody analogues of hCD27.15 which may comprise these CDR sequences, or sequence variants thereof, are particularly considered for use in the invention.

The heavy chain CDR1, CDR2 and CDR3 amino acid sequences and light chain CDR1, CDR2 and CDR3 amino acid sequences of 1F5, identifying the antigen binding region of this antibody, are already disclosed in WO2011/130434. These sequences have also been presented in SEQ ID NO: 11-16 of the sequence listing of this description, together with the amino acid sequences of the heavy chain variable region and the light chain variable region (SEQ ID NO: 17 and 18). Antibody analogues of 1F5 which may comprise these CDR sequences, or sequence variants thereof, are particularly considered for use in the invention.

Alternatively, analogues of hCD27.1.5 or 1F5 binding to the same epitope of these antibodies, but having differing CDRs may also be selected. To screen for antibodies that bind to the hCD27.15 or 1F5 epitope on human CD27, a routine cross-blocking assay such as that described in "Antibodies, A Laboratory Manual, Cold Spring Harbor Laboratory, Ed Harlow and David Lane (1988)", can be performed. Antibodies that bind to the same epitope are likely to cross-block in such assays, but not all cross-blocking antibodies will necessarily bind at precisely the same epitope since cross-blocking may result from steric hindrance of antibody binding by antibodies binding at overlapping epitopes, or even nearby non-overlapping epitopes. Such cross-blocking antibodies maintaining CD27 agonistic functionality are also within the scope of the present invention.

Alternatively, the known technique of epitope mapping, e.g., as described in Champe et al., 1995, *J. Biol. Chem.* 270:1388-1394, can be performed to determine whether the antibody binds an epitope of interest "Alanine scanning mutagenesis," as described by Cunningham and Wells, 1989, *Science* 244: 1081-1085, or some other form of point mutagenesis of amino acid residues in human CD27 may also be used to determine the functional epitope for anti-CD27 antibodies of the present invention.

Another known method to map the epitope of an antibody is to study binding of the antibody to synthetic linear and CLIPS peptides that can be screened using credit-card format mini PEPSCAN cards as described by Slootstra et al. (Slootstra et al., 1996, *Mol. Diversity* 1: 87-96) and Timmerman et al. (Timmerman et al., 2007, *J. Mol. Recognit.* 20: 283-299). The binding of antibodies to each peptide is determined in a PEPSCAN-based enzyme-linked immuno assay (ELISA).

Additional antibodies binding to the same epitope as hCD27.15 may be obtained with known techniques, for example, by screening of antibodies raised against CD27 for binding to the epitope, or by immunization of an animal with a peptide which may comprise a fragment of human CD27 which may comprise the epitope sequences. Antibodies that bind to the same functional epitope might be expected to exhibit similar biological activities, such as CD27 agonistic activity, and such activities can be confirmed by functional assays of the antibodies. For analogues of 1F5 binding to the same epitope of this antibody, these techniques can also be used in analogy.

According to an embodiment an analogue of hCD27.15 binding to the same epitope of this antibody, but having differing CDRs may block binding of hCD27.15 to human CD27 with an $IC_{50}$ of about 50 nM or lower. Alternatively an analogue of hCD27.15 binding to the same epitope of this antibody, but having differing CDRs may be blocked in its binding to human CD27 by hCD27.15 with an $IC_{50}$ of about 50 nM or lower. Similarly analogues of 1F5 binding to the same epitope of this antibody, but having differing CDRs may block binding of 1F5 to human CD27 with an $IC_{50}$ of about 50 nM or lower or alternatively may be blocked in its binding to human CD27 by 1F5 with an $IC_{50}$ of about 50 nM or lower. About 50 nM or lower is to be understood to include $50*10^{-9}$ to $0.1*10^{-12}$ M, such as $20*10^{-9}$ to $1.0*10^{-11}$ M, $10*10^{-9}$ to $1.0*10^{-10}$ M or $10*10^{-9}$ to $1.0*10^{-19}$.

The differing CDRs may be sequence variants of the known CDRs of the human CD27 binding antibody used in the invention, for example hCD27.15 or 1F5. As used herein, a sequence "variant" refers to a sequence that differs from the disclosed sequence at one or more amino acid residues but which retains the biological activity of the resulting molecule. The invention includes the variants of antibodies explicitly disclosed by the various sequences, for example hCD27.15 or 1F5. For the $V_H$ domain CDR1, CDR2 and CDR3 sequences, according to some embodiments, variant sequences may comprise up to 6 amino acid substitutions, such as 1, 2, 3, 4, 5 or 6 amino acid substitutions, for the CDR1, CDR2 and CDR3 sequences taken together. Similarly for the $V_L$ domain CDR1, CDR2 and CDR3 sequences, according to some embodiments, variant sequences may comprise up to 6 amino acid substitutions, such as 1, 2, 3, 4, 5 or 6 amino acid substitutions, for the CDR1, CDR2 and CDR3 sequences taken together. The skilled person will understand that in particular conservative amino acid substitutions may result in maintaining biological activity. For all amino acid and DNA sequences disclosed, the sequence variants are also envisaged within this invention.

"Conservatively modified variants" or "conservative amino acid substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, The Benjamin/Cummings Pub. Co., p. 224 (4th Edition 1987)). Such exemplary substitutions are preferably made in accordance with those set forth above in Table 2.

TABLE 2

| Exemplary Conservative Amino Acid Substitutions | |
|---|---|
| Original residue | Conservative substitution |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

The anti-human CD27 agonistic antibody of the invention is intended for use in the treatment of a condition ameliorated by stimulation of an immune response, in particular the treatment of conditions which are ameliorated by stimulation of antigen-specific T-lymphocytes. Characteristic of this treatment is that a number of immune checkpoint protein inhibitors is administered. Thus the CD27 agonistic antibody is co-administered with a number of immune checkpoint protein inhibitors. Within the present invention the term "number of" should be understood as meaning at least one or alternatively one or more, such as, 1, 2, 3, 4, 5 or 6.

The term "immune checkpoint protein" is known in the art. Within the known meaning of this term it will be clear to the skilled person that on the level of "immune checkpoint proteins" the immune system provides inhibitory signals to its components in order to balance immune reactions. Known immune checkpoint proteins may comprise CTLA-4, PD1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012. *Nature Rev Cancer* 12:252-264; Mellman et al., 2011. *Nature* 480:480-489).

Within the present invention an immune checkpoint protein inhibitor is any compound inhibiting the function of an immune checkpoint protein. Inhibition includes reduction of function and full blockade. In particular the immune checkpoint protein is a human immune checkpoint protein. Thus the immune checkpoint protein inhibitor preferably is an inhibitor of a human immune checkpoint protein. Immune checkpoint proteins are described in the art (see for instance Pardoll, 2012. *Nature Rev. cancer* 12: 252-264). The designation immune checkpoint includes the experimental demonstration of stimulation of an antigen-receptor triggered T lymphocyte response by inhibition of the immune checkpoint protein in vitro or in vivo, e.g. mice deficient in expression of the immune checkpoint protein demonstrate enhanced antigen-specific T lymphocyte responses or signs of autoimmunity (such as disclosed in Waterhouse et al., 1995. *Science* 270:985-988; Nishimura et al., 1999. *Immunity* 11:141-151). It may also include demonstration of inhibition of antigen-receptor triggered CD4+ or CD8+ T cell responses due to deliberate stimulation of the immune checkpoint protein in vitro or in vivo (e.g. Zhu et al., 2005. *Nature Immunol.* 6:1245-1252).

Preferred immune checkpoint protein inhibitors are antibodies that specifically recognize immune checkpoint proteins. A number of CTLA-4, PD1, PDL-1, PD-L2, LAG-3, BTLA, B7H3, B7H4, TIM3 and KIR inhibitors are known and in analogy of these known immune checkpoint protein inhibitors, alternative immune checkpoint inhibitors may be developed in the (near) future. For example ipilimumab is a fully human CTLA-4 blocking antibody presently marketed under the name Yervoy (Bristol-Myers Squibb). A second CTLA-4 inhibitor is tremelimumab (referenced in Ribas et al, 2013, *J. Clin. Oncol.* 31:616-22). Examples of PD-1 inhibitors include without limitation humanized antibodies blocking human PD-1 such as lambrolizumab (e.g. disclosed as hPD109A and its humanized derivatives h409A11, h409A16 and h409A17 in WO2008/156712; Hamid et al., *N. Engl. J. Med.* 369: 134-144 2013,), or pidilizumab (disclosed in Rosenblatt et al., 2011. *J. Immunother.* 34:409-18), as well as fully human antibodies such as nivolumab (previously known as MDX-1106 or BMS-936558, Topalian et al., 2012. *N. Eng. J. Med.* 366:2443-2454, disclosed in U.S. Pat. No. 8,008,449 B2). Other PD-1 inhibitors may include presentations of soluble PD-1 ligand including without limitation PD-L2 Fc fusion protein also known as B7-DC-Ig or AMP-244 (disclosed in Mkrtichyan M, et al. *J Immunol.* 189:2338-47 2012) and other PD-1 inhibitors presently under investigation and/or development for use in therapy. In addition, immune checkpoint inhibitors may include without limitation humanized or fully human antibodies blocking PD-L such as MEDI-4736 (disclosed in WO2011066389 A1), MPDL3280A (disclosed in U.S. Pat. No. 8,217,149 B2) and MIH1 (Affymetrix obtainable via eBioscience (16.5983.82)) and other PD-L1 inhibitors presently under investigation. According to this invention an immune checkpoint inhibitor is preferably selected from a CTLA-4, PD-1 or PD-L1 inhibitor, such as selected from the known CTLA-4, PD-1 or PD-L1 inhibitors mentioned above (ipilimumab, tremelimumab, labrolizumab, nivolumab, pidilizumab, AMP-244, MEDI-4736, MPDL3280A, MIH1). Known inhibitors of these immune checkpoint proteins may be used as such or analogues may be used, in particular chimerized, humanized or human forms of antibodies.

As the skilled person will know, alternative and/or equivalent names may be in use for certain antibodies mentioned above. Such alternative and/or equivalent names are interchangeable in the context of the present invention. For example it is known that lambrolizumab is also known under the alternative and equivalent names MK-3475 and pembrolizumab.

The selection of an immune checkpoint inhibitor from PD1 and PD-L1 inhibitors, such as a known PD-1 or PD-L1 inhibitor mentioned above, is more preferred and most preferably a selection is made from a PD-1 inhibitor, such as a known PD1 inhibitor mentioned above. In preferred embodiments, the PD1 inhibitor is nivolumab or pembrolizumab or another antagonist antibody against human PD1.

The invention also includes the selection of other immune checkpoint inhibitors that are known in the art to stimulate immune responses. This includes inhibitors that directly or indirectly stimulate or enhance antigen-specific T-lymphocytes. These other immune checkpoint inhibitors include, without limitation, agents targeting immune checkpoint proteins and pathways involving PD-L2, LAG3, BTLA, B7H4 and TIM3. For example, human PD-L2 inhibitors known in the art include MIH18 (disclosed in (Pfistershammer et al., 2006. Eur J Immunol. 36:1104-13). Another example, LAG3 inhibitors known in the art include soluble LAG3 (IMP321, or LAG3-Ig disclosed in WO2009044273 A2, and in Brignon et al. 2009. Clin. Cancer Res. 15:6225-6231) as well as mouse or humanized antibodies blocking human LAG3 (for instance IMP701 disclosed in and derived from WO2008132601 A1), or fully human antibodies blocking human LAG3 (such as disclosed in EP 2320940 A2). Another example is provided by the use of blocking agents towards BTLA, including without limitation antibodies blocking human BTLA interaction with its ligand (such as 4C7 disclosed in WO2011014438). Yet another example is provided by the use of agents neutralizing B7H4 including without limitation antibodies to human B7H4 (disclosed in WO 2013025779 A1, and in WO 2013067492 A1) or soluble recombinant forms of B7H4 (such as disclosed in US20120177645 A1 or Anti-human B7H4 clone H74: eBioscience #14-5948). Yet another example is provided by agents neutralizing B7-H3, including without limitation antibodies neutralizing human B7-H3 (e.g. MGA271 disclosed as BRCA84D and derivatives in US 20120294796 A1). Yet another example is provided by agents targeting TIM3, including without limitation antibodies targeting human TIM3 (e.g. as disclosed in WO 2013006490 A2 or the anti-human TIM3, blocking antibody F38-2E2 disclosed by Jones et al., J Exp Med. 2008 Nov. 24; 205(12):2763-79).

Known inhibitors of immune checkpoint proteins may be used in their known form or analogues may be used, in particular chimerized forms of antibodies, most preferably humanized forms.

The invention also includes the selection of more than one immune checkpoint inhibitor selected from CTLA-4, PD-1 or PDL1 inhibitors for combination with an anti-human CD27 agonistic antibody within the various aspects of the invention. For example concurrent therapy of ipilimumab (anti-CTLA4) with Nivolumab (anti-PD1) has demonstrated clinical activity that appears to be distinct from that obtained in monotherapy (Wolchok et al., 2013, *N. Eng. J. Med.,* 369:122-33). Also included are combinations of agents that have been shown to improve the efficacy of checkpoint inhibitors, such as Lirilumab (also known as anti-KIR, BMS-986015 or IPH2102, as disclosed in U.S. Pat. No. 8,119,775 B2 and Benson et al., Blood 120:4324-4333 (2012)) in combination with ipilimumab (Rizvi et at, ASCO 2013, and clinicaltrials.gov NCT01750580) or in combination with nivolumab (Sanborn et al., ASCO 2013, and clinicaltrials.gov NCT01714739), agents targeting LAG3 combined with anti-PD-1 (Woo et al., 2012 Cancer Res. 72:917-27) or anti-PD-L1 (Butler N S et al., Nat Immunol. 2011 13:188-95), agents targeting ICOS in combination with anti-CTLA-4 (Fu et al., Cancer Res. 2011 71:5445-54, or agents targeting 4-1BB in combination with anti-CTLA-4 (Curran et al., PLoS One. 2011 6(4):e19499). Combinations of anti-human CD27 agonistic antibodies and immune checkpoint inhibitors envisaged within the various embodiments of the present invention include those presented in Table 3. In this table the names of anti-human CD27 agonistic antibodies and immune checkpoint inhibitors refers to both the known compound and analogues thereof. For antibodies, analogues include analogues having modified Fc-function, chimerized antibodies and humanized antibodies. For antibodies preferably human or humanized forms are selected. CD27 agonist refers to an anti-human CD27 agonistic antibody.

TABLE 3

COMBINATIONS OF ANTI-HUMAN CD27 AGONISTS AND IMMUNE CHECKPOINT PROTEIN INHIBITORS

| | CTLA-4 inhibitor | Ipilimumab | tremelimumab | PD-1 inhibitor | Lambrolizumab (pembrolizumab/MK-3475) | Nivolumab | pidilizumab | AMP244 | PD-L1 inhibitor | MEDI-4736 | MPDL3280A | MIH1 | PD-L2 inhibitor | MIH18 | KIR inhibitor, e.g. lirilumab | LAG-3 inhibitor, e.g. IMP321, IMP701 | BTLA inhibitor, e.g. 4C7 | B7H4 inhibitor, e.g. H74, soluble B7H4 | B7H3 inhibitor, e.g. MA271 | TIM3 inhibitor, e.g. F38-2E2 |
|---|---|---|---|---|---|---|---|---|---|---|---|---|---|---|---|---|---|---|---|---|
| hCD27.15 | 1 | | | | | | | | | | | | | | | | | | | |
| hCD27.15 | | 1 | | | | | | | | | | | | | | | | | | |
| hCD27.15 | | | 1 | | | | | | | | | | | | | | | | | |
| hCD27.15 | | | | 1 | | | | | | | | | | | | | | | | |
| hCD27.15 | | | | | 1 | | | | | | | | | | | | | | | |
| hCD27.15 | | | | | | 1 | | | | | | | | | | | | | | |
| hCD27.15 | | | | | | | 1 | | | | | | | | | | | | | |
| hCD27.15 | | | | | | | | 1 | | | | | | | | | | | | |
| hCD27.15 | | | | | | | | | 1 | | | | | | | | | | | |
| hCD27.15 | | | | | | | | | | 1 | | | | | | | | | | |
| hCD27.15 | | | | | | | | | | | 1 | | | | | | | | | |
| hCD27.15 | | | | | | | | | | | | 1 | | | | | | | | |
| hCD27.15 | | | | | | | | | | | | | 1 | | | | | | | |
| hCD27.15 | 2 | 2 | | 2 | | | | | | | | | | | | | | | | |
| hCD27.15 | 2 | | 2 | 2 | | | | | | | | | | | | | | | | |
| hCD27.15 | 2 | | | 2 | 2 | | | | | | | | | | | | | | | |
| hCD27.15 | 2 | 2 | | | | 2 | | | | | | | | | | | | | | |
| hCD27.15 | 2 | | 2 | | | 2 | | | | | | | | | | | | | | |
| hCD27.15 | 2 | | | | | 2 | 2 | | | | | | | | | | | | | |
| hCD27.15 | 2 | 2 | | | | | | 2 | | | | | | | | | | | | |
| hCD27.15 | 2 | | 2 | | | | | 2 | | | | | | | | | | | | |
| hCD27.15 | 2 | | | | | | | 2 | 2 | | | | | | | | | | | |
| hCD27.15 | 2 | 2 | | | | | | | | 2 | | | | | | | | | | |
| hCD27.15 | 2 | | 2 | | | | | | | 2 | | | | | | | | | | |
| hCD27.15 | 2 | | | | | | | | | 2 | 2 | | | | | | | | | |
| hCD27.15 | | | | | | | | | | | | 2 | | | | | | | | |
| hCD27.15 | | | | | | | | | | | | 2 | | | | | | | | |
| hCD27.15 | | | | | | | | | | | | 2 | | | | | | | | |
| hCD27.15 | | | | | | | | | | | | | | | 1 | | | | | |
| hCD27.15 | | | | | | | | | | | | | | | | 1 | | | | |

TABLE 3-continued

COMBINATIONS OF ANTI-HUMAN CD27 AGONISTS AND IMMUNE CHECKPOINT PROTEIN INHIBITORS

| | CTLA-4 inhibitor | Ipilimumab | tremelimumab | PD-1 inhibitor | Lambrolizumab (pembrolizumab/MK-3475) | Nivolumab | pidilizumab | AMP244 | PD-L1 inhibitor | MEDI-4736 | MPDL3280A | MIH1 | PD-L2 inhibitor MIH18 | KIR inhibitor e.g. lirilumab | LAG-3 inhibitor e.g. IMP321, IMP701 | BTLA inhibitor e.g. 4C7 | B7H4 inhibitor e.g. H74, soluble B7H4 | B7H3 inhibitor e.g. MA271 | TIM3 inhibitor e.g. F38-2E2 |
|---|---|---|---|---|---|---|---|---|---|---|---|---|---|---|---|---|---|---|---|
| hCD27.15 | | | | | | | | | | | | | | | | 1 | | | |
| hCD27.15 | | | | | | | | | | | | | | | | | | 1 | 1 |
| hCD27.15 | | | | | | | | | | | | | | | | | 1 | | |
| hCD27.15 | 2 | | | | | | | | | | | | | | | | | | |
| hCD27.15 | | 2 | | | | | | | | | | | | | | | | | |
| hCD27.15 | | | 2 | | | | | | | | | | | | | | | | |
| hCD27.15 | | | | | 2 | | | | | | | | | | | | | | |
| hCD27.15 | | | | | | 2 | | | | | | | | | | | | | |
| hCD27.15 | | | | | | | 2 | | | | | | | | | | | | |
| hCD27.15 | | | | | | | | 2 | | | | | | | | | | | |
| hCD27.15 | | | | | | | | | 2 | | | | | | | | | | |
| hCD27.15 | | | | | | | | | | 2 | | | | | | | | | |
| hCD27.15 | | | | | | | | | | | 2 | | | | | | | | |
| hCD27.15 | | | | | | | | | | | | 2 | | | | | | | |
| hCD27.15 | | | | | | | | | | | | | | 2 | 2 | | | | |
| hCD27.15 | 2 | | | | | | | | | | | | | 2 | 2 | | | | |
| hCD27.15 | | 2 | | | | | | | | | | | | 2 | 2 | | | | |
| hCD27.15 | | | 2 | | | | | | | | | | | 2 | 2 | | | | |
| hCD27.15 | | | | | 2 | | | | | | | | | 2 | 2 | | | | |
| hCD27.15 | | | | | | 2 | | | | | | | | 2 | 2 | | | | |
| hCD27.15 | | | | | | | 2 | | | | | | | 2 | 2 | | | | |
| hCD27.15 | | | | | | | | 2 | | | | | | 2 | 2 | | | | |
| hCD27.15 | | | | | | | | | 2 | | | | | 2 | 2 | | | | |
| hCD27.15 | | | | | | | | | | 2 | | | | 2 | 2 | | | | |
| hCD27.15 | | | | | | | | | | | 2 | | | 2 | 2 | | | | |
| hCD27.15 | | | | | | | | | | | | 2 | | 2 | 2 | | | | |
| hCD27.15 | 1 | | | | | | | | | | | | | | | | | | |
| 1F5 | | 1 | | | | | | | | | | | | | | | | | |
| 1F5 | | | 1 | | | | | | | | | | | | | | | | |
| 1F5 | | | | 1 | | | | | | | | | | | | | | | |
| 1F5 | | | | | 1 | | | | | | | | | | | | | | |
| 1F5 | | | | | | 1 | | | | | | | | | | | | | |
| 1F5 | | | | | | | 1 | | | | | | | | | | | | |
| 1F5 | | | | | | | | 1 | | | | | | | | | | | |
| 1F5 | | | | | | | | | 1 | | | | | | | | | | |
| 1F5 | | | | | | | | | | 1 | | | | | | | | | |
| 1F5 | | | | | | | | | | | 1 | | | | | | | | |
| 1F5 | | | | | | | | | | | | 1 | | | | | | | |
| 1F5 | 2 | | | | | 2 | | | | | | | | | | | | | |

TABLE 3-continued

COMBINATIONS OF ANTI-HUMAN CD27 AGONISTS AND IMMUNE CHECKPOINT PROTEIN INHIBITORS

| | CTLA-4 inhibitor | Ipilimumab | Tremelimumab | PD-1 inhibitor | Lambrolizumab (pembrolizumab/MK-3475) | Nivolumab | Pidilizumab | AMP244 | PD-L1 inhibitor | MEDI-4736 | MPDL3280A | MIH1 | PD-L2 inhibitor MIH18 | KIR inhibitor, e.g. lirilumab | LAG-3 inhibitor, e.g. IMP321, IMP701 | BTLA inhibitor, e.g. 4C7 | B7H4 inhibitor, e.g. H74, soluble B7H4 | B7H3 inhibitor, e.g. MA271 | TIM3 inhibitor, e.g. F38-2E2 |
|---|---|---|---|---|---|---|---|---|---|---|---|---|---|---|---|---|---|---|---|
| 1F5 | | 2 | | | | | | | | | | | | | | | | | |
| 1F5 | | | | 2 | | | | | | | | | | | | | | | |
| 1F5 | 2 | | | | 2 | | | | | | | | | | | | | | |
| 1F5 | | 2 | | | 2 | | | | | | | | | | | | | | |
| 1F5 | | | 2 | | 2 | | | | | | | | | | | | | | |
| 1F5 | 2 | | | | | 2 | | | | | | | | | | | | | |
| 1F5 | | 2 | | | | 2 | | | | | | | | | | | | | |
| 1F5 | | | 2 | | | 2 | | | | | | | | | | | | | |
| 1F5 | 2 | | | | | | 2 | | | | | | | | | | | | |
| 1F5 | | 2 | | | | | 2 | | | | | | | | | | | | |
| 1F5 | | | 2 | | | | 2 | | | | | | | | | | | | |
| 1F5 | 2 | | | | | | | 2 | | | | | | | | | | | |
| 1F5 | | 2 | | | | | | 2 | | | | | | | | | | | |
| 1F5 | | | 2 | | | | | 2 | | | | | | | | | | | |
| 1F5 | 2 | | | | | | | | 2 | | | | | | | | | | |
| 1F5 | | 2 | | | | | | | 2 | | | | | | | | | | |
| 1F5 | | | 2 | | | | | | 2 | | | | | | | | | | |
| 1F5 | 2 | | | | | | | | | 2 | | | | | | | | | |
| 1F5 | | 2 | | | | | | | | 2 | | | | | | | | | |
| 1F5 | | | 2 | | | | | | | 2 | | | | | | | | | |
| 1F5 | 2 | | | | | | | | | | 2 | | | | | | | | |
| 1F5 | | 2 | | | | | | | | | 2 | | | | | | | | |
| 1F5 | | | 2 | | | | | | | | 2 | | | | | | | | |
| 1F5 | 2 | | | | | | | | | | | 2 | | | | | | | |
| 1F5 | | 2 | | | | | | | | | | 2 | | | | | | | |
| 1F5 | | | 2 | | | | | | | | | 2 | | | | | | | |
| 1F5 | | | | | | | | | | | | | | 1 | | | | | |
| 1F5 | | | | | | | | | | | | | | | 1 | | | | |
| 1F5 | | | | | 2 | | | | | | | | | | | 1 | | | |
| 1F5 | | | | | | | | | | | | | | | | | 1 | | |
| 1F5 | | | | | | | | | | | | | | | | | | 1 | |
| 1F5 | | | | | | | | | | | | | | | | | | | 1 |
| 1F5 | | | | | | 2 | | | | | | | | | 2 | | | | |
| 1F5 | | | | 2 | | | | | | | | | | | 2 | | | | |
| 1F5 | | | | | | | 2 | | | | | | | | 2 | | | | |
| 1F5 | | | | | | | | 2 | | | | | | | 2 | | | | |
| 1F5 | | | | | | | | | 2 | | | | | | 2 | | | | |
| 1F5 | | | | | | | | | | 2 | | | | | 2 | | | | |
| 1F5 | | | | | | | | | | | 2 | | | | 2 | | | | |

TABLE 3-continued

COMBINATIONS OF ANTI-HUMAN CD27 AGONISTS AND IMMUNE CHECKPOINT PROTEIN INHIBITORS

| CD27 agonist | CTLA-4 inhibitor | Ipi-limu-mab | treme-limu-mab | PD-1 inhib-itor | Lambro-lizimab (pembro-lizumab/MK-3475) | Nivo-lumab | pidi-lizumab | AMP244 | PD-L1 inhib-itor | MEDI-4736 | MPDL3280A | MIH1 | PD-L2 inhib-itor | MIH18 | KIR inhib-itor e.g. lirilumab | LAG-3 inhib-itor e.g. IMP321, IMP701 | BTLA inhib-itor e.g. 4C7 | B7H4 inhib-itor, e.g. H74, soluble B7H4 | B7H3 inhib-itor, e.g. MA271 | TIM3 inhib-itor, e.g. F38-2E2 |
|---|---|---|---|---|---|---|---|---|---|---|---|---|---|---|---|---|---|---|---|---|
| 1F5 | 2 | | | | | | | | | | | | | | | | | | | |
| 1F5 | | 2 | | | | | | | | | | | | | | | | | | |
| 1F5 | | | 2 | | | | | | | | | | | | | | | | | |
| 1F5 | | | | 2 | | | | | | | | | | | | | | | | |
| 1F5 | | | | | 2 | | | | | | | | | | | | | | | |
| 1F5 | | | | | | 2 | | | | | | | | | | | | | | |
| 1F5 | | | | | | | 2 | | | | | | | | | | | | | |
| 1F5 | | | | | | | | 2 | | | | | | | | | | | | |
| 1F5 | | | | | | | | | 2 | | | | | | | | | | | |
| 1F5 | | | | | | | | | | 2 | | | | | | | | | | |
| 1F5 | | | | | | | | | | | 2 | | | | | 2 | | | | |
| CD27 agonist | 1 | 1 | | | | | | | | | | | | | | | | | | |
| CD27 agonist | | | 1 | | | | | | | | | | | | 2 | | | | | |
| CD27 agonist | | | | 1 | | | | | | | | | | | 2 | | | | | |
| CD27 agonist | | | | | 1 | | | | | | | | | | 2 | | | | | |
| CD27 agonist | | | | | | 1 | | | | | | | | | 2 | | | | | |
| CD27 agonist | | | | | | | 1 | | | | | | | | 2 | | | | | |
| CD27 agonist | | | | | | | | 1 | | | | | | | 2 | | | | | |
| CD27 agonist | | | | | | | | | 1 | | | | | | 2 | | | | | |
| CD27 agonist | 2 | 2 | 2 | 2 | 2 | 2 | 2 | 2 | | | | | | | | | | | | |
| CD27 agonist | 2 | 2 | 2 | 2 | 2 | 2 | 2 | 2 | | | | | | | | | | | | |
| CD27 agonist | 2 | 2 | 2 | 2 | 2 | 2 | 2 | 2 | | | | | | | | | | | | |
| CD27 agonist | 2 | 2 | | | | | | | 2 | | | | | | | | | | | |
| CD27 agonist | 2 | 2 | | | | | | | 2 | | | | | | | | | | | |
| CD27 agonist | 2 | 2 | | | | | | | 2 | | | | | | | | | | | |

TABLE 3-continued

COMBINATIONS OF ANTI-HUMAN CD27 AGONISTS AND IMMUNE CHECKPOINT PROTEIN INHIBITORS

| | CTLA-4 inhibitor | Ipilimumab | tremelimumab | PD-1 inhibitor | Lambrolizimab (pembrolizumab/MK-3475) | Nivolumab | pidilizumab | AMP244 | PD-L1 inhibitor | MEDI-4736 | MPDL3280A | MIH1 | PD-L2 inhibitor MIH18 | KIR inhibitor, e.g. lirilumab | LAG-3 inhibitor, e.g. IMP321, IMP701 | BTLA inhibitor, e.g. 4C7 | B7H4 inhibitor, e.g. H74, soluble B7H4 | B7H3 inhibitor, e.g. MA271 | TIM3 inhibitor, e.g. F38-2E2 |
|---|---|---|---|---|---|---|---|---|---|---|---|---|---|---|---|---|---|---|---|
| CD27 agonist | 2 | | | | | | | | | | | | | | | | | | |
| CD27 agonist | | 2 | | | | | | | | 2 | | | | | | | | | |
| CD27 agonist | 2 | | | | | | | | | 2 | | | | | | | | | |
| CD27 agonist | | 2 | | | | | | | | | 2 | | | | | | | | |
| CD27 agonist | 2 | | | | | | | | | | 2 | | | | | | | | |
| CD27 agonist | | | 2 | | | | | | | | 2 | | | | | | | | |
| CD27 agonist | 2 | | | | | | | | | | | 2 | | | | | | | |
| CD27 agonist | | | | | | | | | | | | 2 | | | | | | | |
| CD27 agonist | | | | | | | | | | | | 2 | | | | | | | |
| CD27 agonist | | | | | | | | | | | | | | 1 | | | | | |
| CD27 agonist | | | | | | | | | | | | | | | 1 | | | | |
| CD27 agonist | | 2 | | | 2 | | | | | | | | | | | | | | |
| CD27 agonist | | | 2 | | 2 | | | | | | | | | | | | | | |
| CD27 agonist | 2 | | | | | 2 | | | | | | | | | | | | | |
| CD27 agonist | | | | 2 | | | 2 | | | | | | | | | | | | |
| CD27 agonist | | 2 | | | | | | 2 | | | | | | | | | | | |
| CD27 agonist | | | 2 | | | 2 | | | | | | | | | | | | | |
| CD27 agonist | 2 | | | | | | | | | | | | 2 | | | | | | |
| CD27 agonist | | | | 2 | | | | | | | | | | | | | | | |
| CD27 agonist | | | | | | | 2 | | | | | | | | | | | | |
| CD27 agonist | | | | | | | | 2 | | | | | | | | | | | |
| CD27 agonist | | | | | | | | | 2 | | | | | | | | | | |
| CD27 agonist | | | | | | | | | | | | | | | 2 | | | | |
| CD27 agonist | | | | | | | | | | | | | | 2 | 2 | | | | |
| CD27 agonist | | | | | | | | | | | | | | 2 | 2 | | | | |
| CD27 agonist | | | | | | | | | | | | | | 2 | 2 | | | | |
| CD27 agonist | | | | | | | | | | | | | | 2 | 2 | | | | |
| CD27 agonist | | | | | | | | | | | | | | 2 | 2 | | | | |
| CD27 agonist | | | | | | | | | | | | 2 | | 2 | | | | | |
| CD27 agonist | | | | | | | | | | | | | | | | 1 | | | |
| CD27 agonist | | | | | | | | | | | | | | | | | 1 | | |
| CD27 agonist | | | | | | | | | | | | 2 | | | | | | | |
| CD27 agonist | | | | | | | | | | | | | | | | | | 1 | |
| CD27 agonist | | | | | | | | | | | | | | | | | | | 1 |

In the table above presenting combinations of anti-human CD27 antibodies with Immune checkpoint inhibitors of the invention, numbers indicated (N) refer to the number of immune checkpoint inhibitors (N = 1 or N = 2) combined with an anti-human CD27 agonistic antibody. When a number is presented the combination comprises the immune checkpoint inhibitor(s) listed in the column at the position of the number.

Most of the immune checkpoint protein inhibitors presently known are antibodies. In view of the advances in antibody technology the use of an antibody as an immune checkpoint protein inhibitor is preferred in the present invention. However, the use of alternative immune checkpoint inhibitors based on other technologies is also envisaged in alternative embodiments.

As the skilled person will know other technologies are available for developing binding compounds interfering with the function of proteins such as immune checkpoint proteins and thus acting as an inhibitor. For example as the skilled person will understand, a library of binding peptides engineered on non-immunoglobulin protein scaffolds can be used to select binding peptides that inhibit immune checkpoint proteins. Examples of such protein scaffolds include, but at not restricted to Adnectins, Affibodies, Anticalins and DARPins (Gebauer and Skerra, *Current opinion Chem. Biol.*, 2009, 13:245-255 and Caravella and Lugovskoy, *Current opinion Chem. Biol.*, 2010, 14:520-528). Selection methods for example include phage display to identify protein scaffolds that express peptides binding to immune check point proteins. In addition, combinatorial peptide libraries which may comprise peptides potentially presenting immune checkpoint protein inhibitory functions may be screened for suitable immune checkpoint protein inhibitors. From such a library For example, one-bead-one-compound combinatorial libraries expressing a broad set of peptides on beads, where one bead is binding one peptide, may be used. After selection procedures, beads are recovered and the peptide is identified (Lam et al., *Methods*, 1996, 9:482-93; Xiao et al., *Comb. Chem. High Throughput Screen*, 2013 16:441-8). For example using mass-spectrometry methods.

In the present invention the term "antibody" is used in the broadest sense and specifically covers, but is not limited to, monoclonal antibodies (including full length monoclonal antibodies), polyclonal antibodies, and multispecific antibodies (e.g., bispecific antibodies) and binding fragments thereof.

"Antibody fragment" and "antibody binding fragment" mean antigen-binding fragments of an antibody, typically including at least a portion of the antigen binding or variable regions (e.g. one or more CDRs) of the parental antibody. An antibody fragment retains at least some of the binding specificity of the parental antibody. Typically, an antibody fragment retains at least 10% of the parental binding activity when that activity is expressed on a molar basis. Preferably, an antibody fragment retains at least 20%, 50%, 70%, 80%, 90%, 95% or 100% or more of the parental antibody's binding affinity for the target. Therefore, as is clear for the skilled person, "antibody fragments" in many applications may substitute antibodies and the term "antibody" should be understood as including "antibody fragments" when such a substitution is suitable. Examples of antibody fragments include, but are not limited to, Fab, Fab', F(ab')2, and Fv fragments; diabodies; linear antibodies; single-chain antibody molecules, e.g., sc-Fv, unibodies or duobodies (technology from Genmab); nanobodies (technology from Ablynx); domain antibodies (technology from Domantis); and multispecific antibodies formed from antibody fragments. Engineered antibody variants are reviewed in Holliger and Hudson, 2005, Nat. Biotechnol. 23:1126-1136.

An "Fab fragment" may be comprised of one light chain and the CH1 and variable regions of one heavy chain. The heavy chain of a Fab molecule cannot form a disulfide bond with another heavy chain molecule.

An "Fc" region contains two heavy chain fragments which may comprise the $C_H1$ and $C_H2$ domains of an antibody. The two heavy chain fragments are held together by two or more disulfide bonds and by hydrophobic interactions of the $C_H3$ domains.

An "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

An "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" may comprise the variable regions from both the heavy and light chains, but lacks the constant regions.

A "single-chain Fv antibody" (or "scFv antibody") refers to antibody fragments which may comprise the $V_H$ and $V_L$ domains of an antibody, wherein these domains are present in a single polypeptide chain. Generally, the Fv polypeptide may further comprise a polypeptide linker between the $V_H$ and $V_L$ domains which enables the scFv to form the desired structure for antigen binding. For a review of scFv, see Pluckthun, 1994, The Pharmacology of Monoclonal Antibodies, vol. 113, Rosenburg and Moore eds. Springer-Verlag. New York, pp. 269-315. See also, International Patent Application Publication No. WO 88/01649 and U.S. Pat. Nos. 4,946,778 and 5,260,203.

A "diabody" is a small antibody fragment with two antigen-binding sites. The fragments may comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al., 1993, Proc. Natl. Acad. Sci. USA 90: 6444-6448.

A "domain antibody fragment" is an immunologically functional immunoglobulin fragment containing only the variable region of a heavy chain or the variable region of a light chain. In some instances, two or more $V_H$ regions are covalently joined with a peptide linker to create a bivalent domain antibody fragment. The two $V_H$ regions of a bivalent domain antibody fragment may target the same or different antigens.

An antibody fragment of the invention may comprise a sufficient portion of the constant region to permit dimerization (or multimerization) of heavy chains that have reduced disulfide linkage capability, for example where at least one of the hinge cysteines normally involved in inter-heavy chain disulfide linkage is altered with known methods available to the skilled person. In another embodiment, an antibody fragment, for example one that may comprise the Fc region, retains at least one of the biological functions normally associated with the Fc region when present in an intact antibody, such as FcRn binding, antibody half life modulation, ADCC (antibody dependent cellular cytotoxicity) function, and/or complement binding (for example, where the antibody has a glycosylation profile necessary for ADCC function or complement binding).

The antibody is directed against human CD27 and thus may comprise binding domains that bind to and/or interact with human CD27. The antibody may be raised in an animal from a non-human species suitable for eliciting antibodies against human antigens. Alternatively, the antibody may be isolated from antibody phage libraries generated using the techniques described in McCafferty et al., 1990, *Nature*, 348:552-554. Clackson et al., 1991, *Nature*, 352:624-628, and Marks et al., 1991, *J. Mol. Biol.* 222:581-597. The skilled person will be able to select a suitable non-human species for eliciting antibodies against human antigens. For example a selection may be made from a non-human mammal, such as a rodent, including murine (rat or mouse) or hamster species, or alternatively a camelid species.

The antibody, when raised in a non-human species, preferably is chimerized with methods and techniques known in the art to form a "chimeric antibody". The term "chimeric" antibody refers to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (See, for example, U.S. Pat. No. 4,816,567 and Morrison et al., 1984, Proc. Natl. Acad. Sci. USA 81:6851-6855). Within the present invention a "chimeric antibody" preferably is a "humanized antibody".

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody may comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also may comprise at least a portion of an immunoglobulin constant region (Fc), typically that of a human immunoglobulin. The humanized forms of rodent antibodies may essentially comprise the same CDR sequences of the parental rodent antibodies, although certain amino acid substitutions may be included to increase affinity, increase stability of the humanized antibody, or for other reasons However, as CDR loop exchanges do not uniformly result in an antibody with the same binding properties as the antibody of origin, changes in framework residues (FR), residues involved in CDR loop support, might also be introduced in humanized antibodies to preserve antigen binding affinity (Kabat et al., 1991, J. Immunol. 147:1709).

The term "antibody" also includes "fully human" antibodies, i.e., antibodies that may comprise human immunoglobulin protein sequences only. A fully human antibody may contain non-human, such as murine (rat or mouse) carbohydrate chains if produced in a non-human cell (e.g. mouse or hamster), or in a hybridoma derived from a murine cell. Similarly, "mouse antibody" or "rat antibody" refer to an antibody that may comprise only mouse or rat immunoglobulin sequences, respectively.

A fully human antibody may be generated in a human being, in a transgenic non-human animal having human immunoglobulin germline sequences, by phage display or other molecular biological methods. Also, recombinant immunoglobulins may also be made in transgenic mice. See Mendez et al., 1997, Nature Genetics 15:146-156. See also Abgenix, Medarex, MeMo and Kymab technologies.

The antibodies of the present invention also include antibodies with modified (or blocked) Fc regions to provide altered effector functions. See, e.g. U.S. Pat. No. 5,624,821; WO2003/086310; WO2005/120571; WO2006/0057702; Presta, 2006, *Adv. Drug Delivery Rev.* 58:640-656; Vincent and Zurini, *Biotechnol. J.*, 2012, 7:1444-50; Kaneko and Niwa, *Biodrugs*, 2011, 25: 1-11. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Preferably, Fc regions displaying reduced Fc effector functions are used. The antibodies of the present invention also include antibodies that have a human IgG4 containing Fc regions. And/or Fc regions carrying a N297Q glycosylation deficient mutant are used.

Changes to the Fc can also alter the half-life of antibodies in therapeutic antibodies, and a longer half-life would result in less frequent dosing, with the concomitant increased convenience and decreased use of material. See Presta, 2005, J. Allergy Clin. Immunol. 116:731 at 734-35.

The antibodies of the present invention, although less preferred, also include antibodies with intact Fc regions that provide full effector functions, e.g. antibodies of isotype IgG1, which induce complement-dependent cytotoxicity (CDC) or antibody dependent cellular cytotoxicity (ADCC) in the a cell associated with the target for the antibody.

The antibodies may also be conjugated (e.g., covalently linked) to molecules that improve stability of the antibody during storage or increase the half-life of the antibody in vivo. Examples of molecules that increase the half-life are albumin (e.g., human serum albumin) and polyethylene glycol (PEG). Albumin-linked and PEGylated derivatives of antibodies can be prepared using techniques well known in the art. See, e.g. Chapman, 2002, Adv. Drug Deliv. Rev. 54:531-545; Anderson and Tomasi, 1988, J. Immunol. Methods 109:37-42; Suzuki et al., 1984, Biochim. Biophys. Acta 788:248-255; and Brekke and Sandlie, 2003, Nature Rev. 2:52-62.

As used herein, the term "about" refers to a value that is within an acceptable error range for the particular value as determined by one of ordinary skill in the art, which will depend in part on how the value is measured or determined, i.e. the limitations of the measurement system. For example, "about" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

The antibody can be selected from any class of immunoglobulins, including IgM, IgG, IgD, IgA, and IgE. Preferably, the antibody is an IgG antibody. Any isotype of IgG can be used, including IgG1, IgG2, IgG3, and IgG4. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described in the Examples.

Likewise, either class of light chain can be used in the compositions and methods herein. Specifically, kappa, lambda, or variants thereof are useful in the present compositions and methods.

The term "monoclonal antibody" as used herein refers to an antibody obtained from a population of substantially homogeneous antibodies, i.e., the individual antibodies which may comprise the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975, *Nature* 256:495, or may be made by recombinant DNA methods (see, for example, U.S. Pat. No. 4,816,567). The "monoclonal antibodies" may also be isolated from phage antibody libraries using the techniques described in Clackson et al., 1991, *Nature* 352:624-628 and Marks et al., 1991, *J. Mol. Biol.* 222:581-597, for example. The monoclonal antibodies herein specifically include "chimeric" antibodies.

Monoclonal antibodies can be made according to knowledge and skill in the art of injecting test subjects with human antigen and then generating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA.

For therapeutic applications the antibodies may be used as such or as a treatment conjugate. As used herein, a treatment "conjugate" refers to an antibody, or a fragment thereof, conjugated to a therapeutic moiety, such as a bacterial toxin, a cytotoxic drug or a radiotoxin. Toxic moieties can be conjugated to antibodies, of the invention using methods available in the art.

In view of the fact that the present invention resides in the surprising immune stimulatory effects of the combination of an anti-human CD27 agonistic antibody together with an immune checkpoint inhibitor, the present invention, in its various embodiments is suitable for treatment of a condition known or expected to be ameliorated by immune stimulation, in particular stimulation of antigen-specific T-lymphocytes. In this invention the term antigen-specific T-lymphocyte in particular includes CD4+ and/or CD8+ T cells.

The immune stimulation, in particular the stimulation of antigen-specific T-lymphocytes, may be achieved by stimulation of $CD27^+$ immune cells or by inhibition of an immune checkpoint protein, such as CTLA-4, PD1, PD-L1, PD-L2, LAG-3, BTLA, B7H3, B7H4, TIM3 and KIR. Thus according to certain embodiments the present invention, is suitable for treatment of a condition known or expected to be ameliorated by stimulation of $CD27^+$ immune cells. According to certain alternative embodiments the present invention, is suitable for treatment of a condition known or expected to be ameliorated by inhibition of an immune checkpoint protein, such as CTLA-4, PD1, PD-L1, PD-L2, LAG-3, BTLA, B7H3, B7H4, TIM3 or KIR.

The meaning of the term stimulation in the context of an immune response will be known to the skilled person. It will be clear that this term includes enhancement and thus relates to both elevation of existing immune responses and induction or de novo generation of an immune response.

The skilled person will know which cells are associated with CD27, CTLA-4, PD1, PD-L1, PD-L2, LAG-3, BTLA, B7H3, B7H4, TIM3 and KIR. In particular it is known that CD27 positive cells may or may not express on their cell surface CTLA-4, PD1, PD-L1, PD-L2, LAG-3, BTLA, B7H3, B7H4, TIM3 and KIR (and vice versa). Thus conditions treatable within the present invention are most certainly not restricted to conditions involving cells expressing both CD27 and an immune checkpoint protein, such as CTLA-4, PD-1 or PD-L1, PD-L2, LAG-3, BTLA, B7H3, B7H4, TIM3 or KIR.

The various aspects of the invention are aimed at "treatment of a condition amelioratated by stimulation of an immune response, in particular stimulation of antigen-specific T-lymphocytes". "The treatment of a condition amelioratated by stimulation of an immune response, in particular stimulation of antigen-specific T-lymphocytes" may alternatively be defined as "a treatment wherein stimulation of an immune response, in particular stimulation of antigen-specific T-lymphocytes, is beneficial". The terms "amelioration" and "beneficial" in the context of treatment both refer to clinically meaning full improvement as can be predicted and/or established by a physician.

Within the present invention the treatment of the "condition" includes any therapeutic use including prophylactic and curative uses of the anti-human CD27 agonistic antibody and the number of immune checkpoint inhibitors. Therefore the term "condition" may refer to disease states but also to physiological states in the prophylactic setting where physiology is not altered to a detrimental state. Conditions in the setting of prophylactic use of the anti-human CD27 agonistic antibody and the number of immune checkpoint inhibitors include for example immunization (the physiological process of inducing and/or generating immune memory against an antigen) after vaccination. The treatment within the context of the present invention thus may be aimed at supporting prophylactically induced physiological processes.

Conditions ameliorated by immune stimulation, in particular stimulation of antigen-specific T-lymphocytes include infectious diseases, such as bacterial, fungal, viral and parasitic infectious diseases. In addition immunization after vaccination may also be ameliorated by immune stimulation, in particular stimulation of antigen-specific T-lymphocytes. The vaccination may be against a pathogen, such as pathogen selected from bacteria, fungi, viruses or parasites, or against toxins, or self-antigens, including antigens expressed on benign or malignant tumors, including cancers. Also conditions associated with uncontrolled proliferation of cells such as cancers may be ameliorated by immune stimulation, in particular stimulation of antigen-specific T-lymphocytes. These conditions may be ameliorated by stimulation of CD27 immune cells and/or by inhibition of an immune checkpoint protein, such as CTLA-4, PD1, PD-L, PD-L2, LAG-3, BTLA, B7H3, B7H4, TIM3 or KIR.

Cancers within the present invention include, but are not limited to, leukemia, acute lymphocytic leukemia, acute myelocytic leukemia, myeloblasts promyelocyte, myelomonocytic monocytic erythroleukemia, chronic leukemia, chronic myelocytic (granulocytic) leukemia, chronic lymphocytic leukemia, mantle cell lymphoma, primary central nervous system lymphoma. Burkitt's lymphoma and marginal zone B cell lymphoma. Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer(for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system.

Less preferred cancers include CD27-expressing tumors, such as those selected from the group consisting of chronic lymphocytic leukemia, mantle cell lymphoma, primary central nervous system lymphoma, Burkitt's lymphoma and marginal zone B cell lymphoma.

Some examples of pathogenic viruses causing infections ameliorated by immune stimulation, in particular stimulation of antigen-specific T-lymphocytes include HIV, hepatitis (A, B, C, D or E), herpes virus (e.g., VZV, HSV-1, HAV-6. HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections ameliorated by immune stimulation, in particular stimulation of antigen-specific T-lymphocytes, include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme disease bacteria.

Some examples of pathogenic fungi causing infections ameliorated by immune stimulation, in particular stimulation of antigen-specific T-lymphocytes, include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis. Paracoccidioides brasiliensis, Coccidioides immitis* and *Histoplasma capsulatum*.

Some examples of pathogenic parasites causing infections ameliorated by immune stimulation, in particular stimulation of antigen-specific T-lymphocytes, include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

If the condition ameliorated by immune stimulation, in particular stimulation of antigen-specific T-lymphocytes is immunization against an antigen, the anti-human CD27 agonistic antibody and the number of immune checkpoint inhibitors are in general administered in combination with a vaccine. The vaccine may comprise a number of antigen or antigenic determinants specific for, a pathogen, such as a pathogen selected from bacteria, fungi, viruses or parasites, or of a toxin, or a self-antigen, including antigens expressed on benign or malignant tumors, such as cancers. The pathogens and cancers against which the vaccination is directed may be selected as indicated above.

According to certain embodiments the vaccination is directed against HIV, Hepatitis (A, B, C, D, E), Influenza, Herpes, Giardia, Malaria, *Leishmania, Staphylococcus aureus*, or *Pseudomonas Aeruginosa*, preferably HIV. For these pathogens there is currently no effective vaccine, or existing vaccines are less than completely effective.

The inventors of the present invention have found unexpected immune stimulatory effects when combining an anti-human CD27 agonistic antibody and a number of immune checkpoint protein inhibitors, in particular an inhibitor of CTLA4 or PD1, PD-L1, PD-L2, LAG-3, BTLA, B7H3, B7H4, TIM3 or KIR. Tests indicate synergistic and/or potentiating effects of the combinations. Thus according to certain embodiments the anti-human CD27 agonistic antibody is for synergistic and/or potentiating stimulation of the immune response, particularly synergistic and/or potentiating stimulation of antigen-specific T-lymphocytes, together with the number of immune checkpoint inhibitors.

The anti-human CD27 agonistic antibody of the present invention preferably is presented in a composition which may comprise the antibody. The composition may comprise the antibody or antibodies together with a carrier. The composition according to certain embodiments preferably is a pharmaceutical composition.

To prepare pharmaceutical or sterile compositions, the antibody, antibodies or fragment thereof, is admixed with a pharmaceutically acceptable carrier and/or excipient, see, e.g., Remington's Pharmaceutical Sciences and U.S. Pharmacopeia: National Formulary, Mack Publishing Company, Easton, PA (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al., 2001, *Goodman and Gilman's The Pharmacological Basis of Therapeutics*, McGraw-Hill, New York, NY; Gennaro, 2000, Remington: *The Science and Practice of Pharmacy*, Lippincott, Williams, and Wilkins, New York, NY, Avis, et al. (eds.), 1993, *Pharmaceutical Dosage Forms: Parenteral Medications*, Marcel Dekker, NY: Lieberman, et al. (eds.), 1990, *Pharmaceutical Dosage Forms: Tablets*, Marcel Dekker, NY; Lieberman, et al. (eds.), 1990, *Pharmaceutical Dosage Forms: Disperse Systems*, Marcel Dekker, NY; Weiner and Kotkoskie, 2000, *Excipient Toxicity and Safety*, Marcel Dekker, Inc., New York, NY).

Toxicity and therapeutic efficacy of the binding compound, in particular antibody, compositions, administered alone or in combination with another agent, such as the usual anti-cancer drugs, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

Suitable routes of administration include parenteral administration, such as intramuscular, intravenous, or subcutaneous administration and oral administration. Administration of antibodies, used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection. In one embodiment, the binding compound of the invention is administered intravenously. In another embodiment, the binding compound of the invention is administered subcutaneously.

Alternatively, one may administer the antibodies in a local rather than systemic manner, for example, via injection of the antibody or antibodies directly into the site of action, often in a depot or sustained release formulation. Furthermore, one may administer the antibody in a targeted drug delivery system.

Guidance in selecting appropriate doses of antibodies, cytokines, and small molecules are available (see, e.g., Wawrzynczak, 1996, *Antibody Therapy*, Bios Scientific Pub. Ltd. Oxfordshire, UK; Kresina (ed.), 1991. *Monoclonal Antibodies, Cytokines and Arthritis*, Marcel Dekker, New York, NY; Bach (ed.), 1993, *Monoclonal Antibodies and Peptide Therapy in Autoimmune Diseases*, Marcel Dekker, New York, NY; Baert, et al., 2003, *New Engl. J. Med.* 348:601-608; Milgrom, et al., 1999, *New Engl. J. Med.* 341:1966-1973; Slamon, et al., 2001, *New Engl. J. Med.* 344:783-792; Beniaminovitz, et al., 2000, *New Engl. J. Med.* 342:613-619; Ghosh, et al., 2003, *New Engl. J. Med.* 348:24-32; Lipsky, et al., 2000, *New Eng. J. Med.* 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

A preferred dose protocol is one involving the maximal dose or dose frequency that avoids significant undesirable side effects. A total weekly dose is generally at least 0.05 µg/kg body weight, more generally at least 0.2 µg/kg, most generally at least 0.5 µg/kg, typically at least 1 µg/kg, more typically at least 10 µg/kg, most typically at least 100 µg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al., 2003, *New Engl. J. Med.* 349:427-434; Herold, et al., 2002, *New Engl. J. Med.* 346:1692-1698; Liu, et al., 1999, *J. Neurol. Neurosurg. Psych.* 67:451-456; Portielji, et al., 2003, *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis.

"Administration", "therapy" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration", "therapy" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration", "therapy" and "treatment" also mean in vitro and ex vivo treatments, e.g., of a cell, by a reagent, diagnostic, binding composition, or by another cell.

As used herein, "inhibit" or "treat" or "treatment" includes a postponement of development of the symptoms associated with disease and/or a reduction in the severity of such symptoms that will or are expected to develop with said disease. The terms further include ameliorating existing symptoms, preventing additional symptoms, and ameliorating or preventing the underlying causes of such symptoms. Thus, the terms denote that a beneficial result has been conferred on a vertebrate subject with a disease.

As used herein, the term "therapeutically effective amount" or "effective amount" refers to an amount of antibody or antibodies, that when administered alone or in combination with an additional therapeutic agent to a cell, tissue, or subject is effective to prevent or ameliorate the disease or condition to be treated. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent are well known in the art, see, e.g., Hardman, et al. (eds.), 2001, *Goodman and Gilman's The Pharmacological Basis of Therapeutics*, 10th ed., McGraw-Hill, New York, NY; Poole and Peterson (eds.), 2001, *Pharmacotherapeutics for Advanced Practice: A Practical Approach*, Lippincott, Williams & Wilkins, Phila., PA; Chabner and Longo (eds.), 2001, *Cancer Chemotherapy and Biotherapy*, Lippincott, Williams & Wilkins, Phila., PA.

Within the present invention the term 'co-administered' should be understood as meaning that the individual active components (here the anti-human CD27 agonistic antibody and the number of immune checkpoint inhibitors) are administered in the same subject. Such administration may be simultaneously or alternatively the active components may be administered within a time frame of up to 3 months, in view of the fact that most antibody therapeutics, including those targeting immune checkpoint inhibitors and CD27 display a terminal half-life in human subjects of 2-4 weeks. Therefore, pharmacodynamic responses to such antibody may be detectable for months after administration.

The pharmaceutical composition of the invention may also contain other agents, including but not limited to a cytotoxic, chemotherapeutic, cytostatic, anti-angiogenic or antimetabolite agents, a tumor targeted agent, an immune stimulating or immune modulating agent or an antibody conjugated to a cytotoxic, cytostatic, or otherwise toxic agent. The pharmaceutical composition can also be employed with other therapeutic modalities such as surgery, chemotherapy and radiation.

According to a preferred embodiment the anti-human CD27 agonistic antibody is provided, in a pharmaceutical composition which may comprise the anti-human CD27 agonistic antibody together with a pharmaceutically acceptable carrier, said pharmaceutical composition being packed in a container and said container being associated with an information carrier, wherein said information carrier may comprise information indicating the combined use of the anti-human CD27 agonistic antibody, preferably in the pharmaceutical composition, together with an immune checkpoint inhibitor for use in the treatment of a condition ameliorated by stimulation of an immune response, in particular stimulation of antigen-specific T-lymphocytes. The container may be any container suitable for holding a pharmaceutical composition, preferably a sterile pharmaceutical composition, more preferably an injectable pharmaceutical composition. According to a preferred embodiment the container may comprise a unit dosage of the anti-human CD27 agonistic antibody.

The information carrier may be any suitable information carrier such as an object having a surface suitable for carrying information, for example paper or cardboard. Alternatively a data carrier which may comprise machine readable information may be used. The information may be presented in visual form such as in the form of written information or in the form of a number of pictures. Alternatively the information may be presented in a form "readable" by touch, such as in braille. In case the information is on a data carrier which may comprise machine readable information, the information may be stored as machine code or analogous signals which can be converted to visual and/or audio information.

The information carrier and the container which may comprise the pharmaceutical composition are associated such that they can be presented together in a single product. For example they may be associated by being enclosed together in an enclosure, such as a container, including a box.

A further aspect of the invention relates to an immune checkpoint inhibitor for use in the treatment of a condition ameliorated by stimulation of an immune response, in particular the treatment of a condition that benefits from the stimulation of antigen-specific T-lymphocytes, wherein in said treatment an anti-human CD27 agonistic antibody is administered. This immune checkpoint inhibitor together with the anti-human CD27 agonistic antibody forms a therapeutic combination resulting in unexpected immune stimulation. According to certain embodiments the immune checkpoint inhibitor is for synergistic and/or potentiating stimulation of the immune response, particularly synergistic and/or potentiating stimulation of antigen-specific T-lymphocytes, together with the anti-human CD27 agonistic antibody. The technical details of the various features and preferred embodiments of the immune checkpoint inhibitor of the invention is similar to what has already been discussed in connection to the anti-human CD27 agonistic antibody of the invention.

Similar to the anti-human CD27 agonistic antibody, the immune checkpoint inhibitor of the invention may be provided, in a pharmaceutical composition which may comprise the immune check point inhibitor together with a pharmaceutically acceptable carrier, said pharmaceutical composition being packed in a container and said container being associated with an information carrier, wherein said information carrier may comprise information indicating the combined use of the immune checkpoint inhibitor, preferably in the pharmaceutical composition, together with an anti-human CD27 agonistic antibody for use in the treatment of a condition ameliorated by stimulation of an immune response, in particular the treatment of a condition that benefits from stimulation of antigen-specific T-lymphocytes. The container may be any container suitable for holding a pharmaceutical composition, preferably a sterile pharmaceutical composition more preferably an injectable pharmaceutical. According to a preferred embodiment the container may comprise a unit dosage of the anti-human CD27 agonistic antibody. Also for this embodiment of the invention the details of the various technical features and preferred embodiments will be clear from the parts of the description relating to the anti-human CD27 agonistic antibody.

Yet a further aspect of the invention relates to a combination of an anti-human CD27 agonistic antibody together with a number of immune checkpoint inhibitors for use in the treatment of a condition ameliorated by stimulation of an immune response, in particular the treatment of a condition that benefits from the stimulation of antigen-specific T-lymphocytes. This combination according to the invention is primarily a functional combination and any physical combination considered suitable by the skilled person for making this functional combination is to be considered within the scope of this invention. For example in the combination the anti-human CD27 agonistic antibody may be co-administered with the number of immune checkpoint inhibitors to a subject. Alternatively, the combination may be a kit of parts which may comprise:

(i) a first container holding a first pharmaceutical composition which may comprise the anti-human CD27 agonistic antibody together with a pharmaceutically acceptable carrier;

(ii) a second container holding a second pharmaceutical composition which may comprise the immune checkpoint inhibitor together with a pharmaceutically acceptable carrier (iii) optionally an information carrier which may comprise information indicating the combined use of the anti-human CD27 agonistic antibody, preferably in the first pharmaceutical composition, together with an immune checkpoint inhibitor, preferably in the second pharmaceutical composition, for use in the treatment of a condition ameliorated by stimulation of an immune response, in particular the treatment of conditions that benefit from the stimulation or enhancement of antigen-specific T-lymphocytes.

According to an alternative embodiment the first and second container and the first and second pharmaceutical composition coincide thus presenting a kit of parts which may comprise:
(A) a container holding a pharmaceutical composition which may comprise the anti-human CD27 agonistic antibody and the immune checkpoint inhibitor together with a pharmaceutically acceptable carrier;
(B) optionally an information carrier which may comprise information indicating the combined use of the anti-human CD27 agonistic antibody, preferably in the pharmaceutical composition, together with an immune checkpoint inhibitor, preferably in the pharmaceutical composition, for use in the treatment of a condition ameliorated by stimulation of an immune response, in particular the treatment of a condition that benefits from the stimulation of antigen-specific T-lymphocytes.

Also for the combination of the invention the details of the various technical features and preferred embodiments is similar to what has been discussed in the parts of the description relating to the anti-human CD27 agonistic antibody.

A further aspect of the invention relates to a method for treating a condition ameliorated by stimulation of an immune response, in particular the treatments of a condition that result in the stimulation of antigen-specific T-lymphocytes, said method which may comprise administering a CD27 agonist, preferably an anti-human CD27 agonistic antibody, in combination with a number of immune checkpoint inhibitors.

Also for the method of treatment of the invention the details of the various technical features and preferred embodiments are similar to what has been discussed above in relation to the anti-human CD27 agonistic antibody.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Figure 1B:
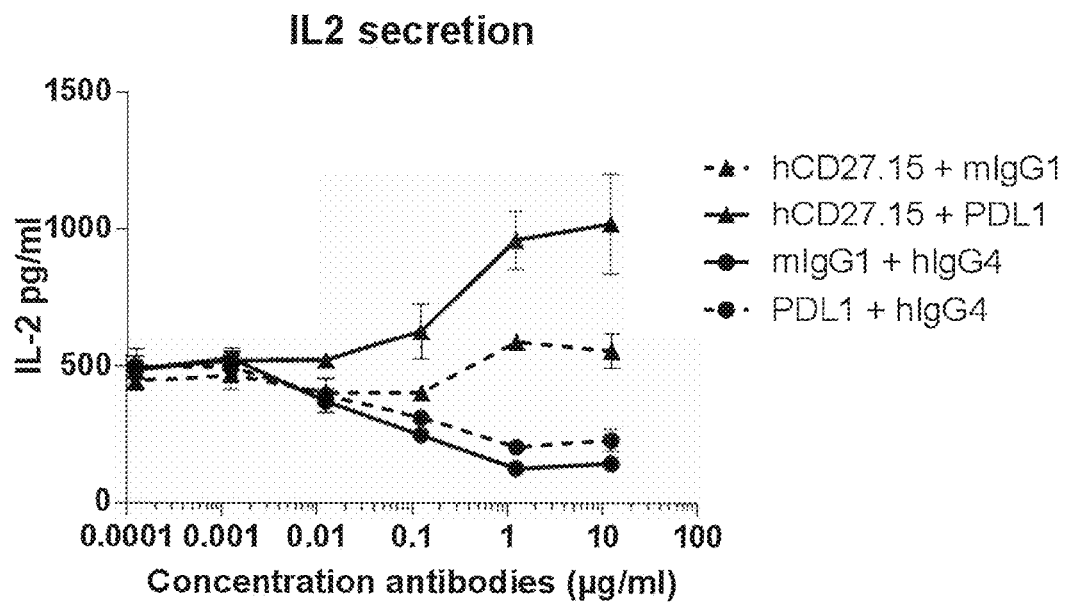

CD27 Agonism Combined with Checkpoint Protein Blockade Results in Unexpected Immune Stimulation To study the effect of combining CD27 agonists with PD-1 or PD-L1 blocking antibodies human Peripheral Blood Mononuclear cells (PBMNCs) were isolated from buffy coat. First, the Buffy coat was diluted to a total volume of 300 ml with DMEM/F12 medium (Gibco, 11320) supplemented with heparin solution (Leo Pharma, DB6132, 5000 U/ml) at RT. After mixing the cell suspension, aliquotes were loaded on a Ficoll-Paque Plus gradient in conical tubes and centrifuged at 450 g for 30 min, at 20° C. without a brake. Next, plasma was removed by aspiration and PBMCs were recovered from the plasma/Ficoll interface. PBMCs were washed twice with DMEM/F12 medium and resuspended in RPMI 1640 medium (Gibco, 52400) supplemented with 10% Foetal Calf Serum PBMCs were plated at $2\times10^5$ cells/well in 96-well flat bottom plates (Nuclon). Antibodies (anti-PD1 (hIgG4 chimera, see below, of hPD109A, WO/2008/156712), anti-hCD27 (hIgG4 chimera of hCD27.15). See below for chimerization), anti-PDL1 (MIH1, eBioscience 16.5983.82), human IgG4 isotype control (Sigma, 14639) and mouse IgG1 isotype control (eBioscience, 16.4714.85)) and dilutions thereof were diluted in PBS and added to the PBMCs. Human IgG4 chimeric versions of hPD1.09A and hCD27.15 were constructed by cloning of the VH and VL genes upstream of the human IgG4 and human Kappa constant domain encoding cDNA, respectively. Full cDNAs were subcloned in pcDNA3.1 (Invitrogen) and transiently transfected in 293T/17 cells (ATCC) using Lipofectamine 2000 (Invitrogen) following the manufacturer's instructions. After 5-7 days, supernatants were harvested and antibodies were purified using standard protein A purification. Finally, *Staphylococcus* Enterotoxin B (Sigma S4881) diluted in RPMI 1640 medium supplemented with 10% Foetal Calf Serum was added to the wells in a final concentration of 25 ng/ml. Cells were incubated for two days at 37° C., 5% $CO_2$ and 95% humidity. To assess the level of immune activation, IL-2 secretion levels were determined in the supernatant in accordance with the method described in Dulos et al., *J. Immunother*, 2012, 35:169-78. To that aim, supernatants were aspirated and cleared from any cell material by centrifugation. Next, supernatants were added to Nunc maxisorp ELISA plates that had been coated with 2 μg/ml anti-hIL-2 antibody (BDPharmingen, 555051) in PBS by overnight incubation at 4° C. Prior to addition of the supernatants, wells were emptied and blocked with 200 μl/well PBS/1% BSA for one hour at Room Temperature (RT). Supernatants were incubated for one hour at RT, washed three times with PBST (PBS with 0.01% Tween 20). Subsequently, 100 μl of 0.5 μg/ml of anti-hIL2-biotin (BD Pharmingen 555040) was added in PBS/PBS-1% BSA (1:1) and incubated for one hour at RT. After three washes with PBST, 1:5000 diluted streptavidin-HRP (BD Pharmingen, 554066) was added in 100 μl PBS/PBS-1% BSA (1:1). After three washes with PBST and one wash with water, IL-2 was detected by addition of 100 μl/well TMB stabilized chromogen (Invitrogen, SB02). Reactions were stopped with 100 μl 0.5 M $H_2SO_4$ and absorbances were read at 450 and 620 nm. In this assay, recombinant human IL-2 (Sigma. H7041) was used to quantify IL-2 protein levels in the supernatants. In FIG. 1A the cooperative action between CD27 agonistic antibody and PD-1 blocking antibody and in FIG. 1B the cooperative action between CD27 agonistic antibody and PD-L11 blocking antibody is shown.

To study the effect of combining CD27 agonist with PD-1 and PD-L1 blocking antibody in whole human blood, blood was diluted 10 times in RPMI 1640 medium (Gibco, 52400) supplemented with 10% Foetal Bovine Serum (Hyclone). Diluted blood was plated in 96-well Nunclon delta surface flat bottom plates (100 μl/well). Antibodies anti-hCD27 (hIgG4 chimera of hCD27.15, see above)), anti-PD-1 (hIgG4 chimera of hPD1.09A, see above), anti-PDL1 (MIH1, eBioscience 16.5983.82), human IgG4 isotype control (Sigma, 14639) and mouse IgG1 isotype control (eBioscience, 16.4714.85) and dilutions thereof were diluted in PBS and added to the diluted blood. Finally, *Staphylococcus* Enterotoxin B (Sigma S4881) diluted in RPMI 1640 medium supplemented with 10% Foetal Calf Serum was added to the wells in a final concentration of 25 ng/ml. Cells were incubated for two days at 37° C., 5% $CO_2$ and 95% humidity. To assess the level of immune activation, IL-2 secretion levels were determined in the supernatant. To that aim, supernatants were aspirated and cleared from any cell material by centrifugation. Next, supernatants were added to Nunc maxisorp ELISA plates that had been coated with 2

µg/ml anti-hIL-2 antibody (BD Pharmingen, 555051) in PBS by overnight incubation at 4° C. Prior to addition of the supernatant, wells were emptied and blocked with 200 µl/well PBS/1% BSA for one hour at Room Temperature (RT). Supernatants were incubated for one hour at RT, washed three times with PBST (PBS with 0.01% Tween 20). Subsequently, 100 µl of 0.5 µg/ml of anti-hIL2-biotin (BD Pharmingen 555040) was added in PBS/PBS-1% BSA (1:1) and incubated for one hour at RT. After three washes with PBST, 1:5000 diluted streptavidin-HRP (BD Pharmingen, 554066) was added in 100 µl PBS/PBS-1% BSA (1:1). After three washes with PBST and one wash with water, IL-2 was detected by addition of 100 µl/well TMB stabilized chromogen (Invitrogen. SB02). Reactions were stopped with 100 µl 0.5 M $H_2SO_4$ and absorbances were read at 450 and 620 nm. In this assay, recombinant human IL-2 (Sigma, 1H7041) was used to quantify IL-2 protein levels in the supernatants. Also in this test the IL-2 level was increased to an unexpected level by the combination of the CD27 agonistic antibody and the PD-1 or PDL-1 inhibiting antibody in comparison to these antibodies alone.

Figure 2A:
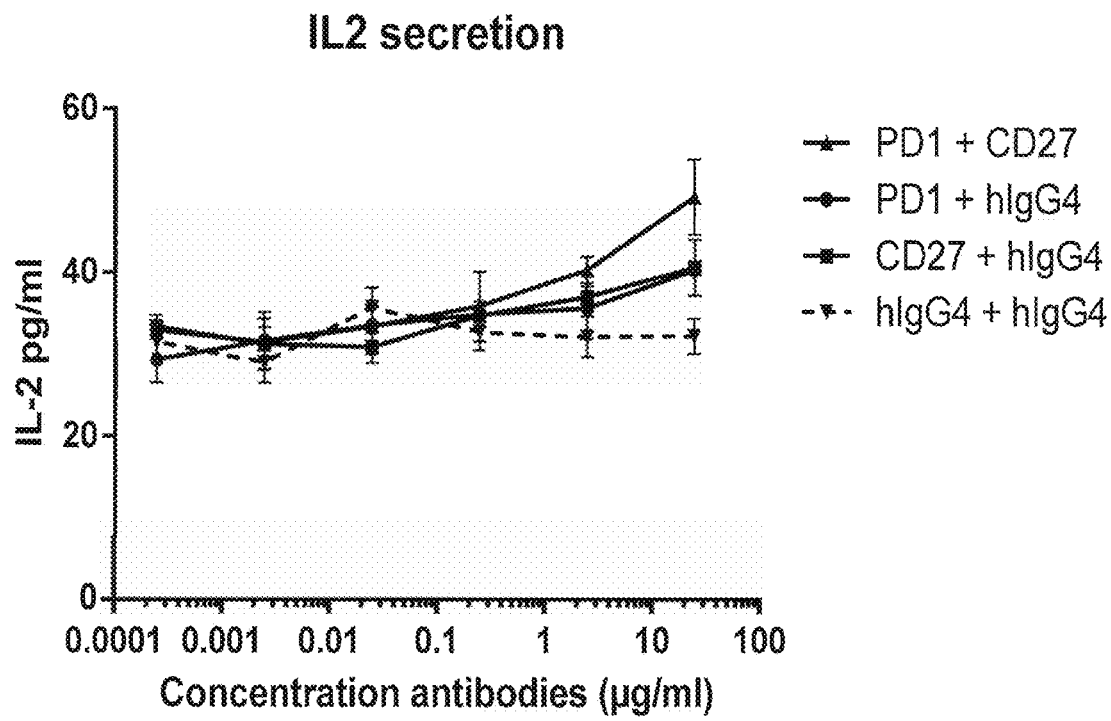
FIGS. 2A-C.
Figure 2B:
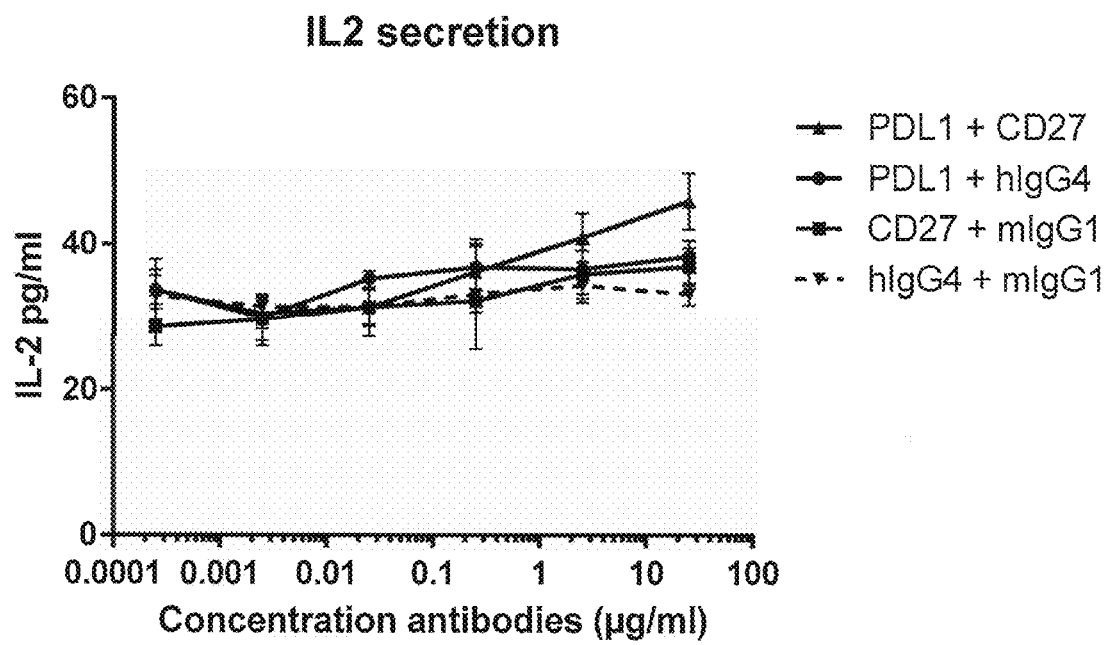
Figure 2C:
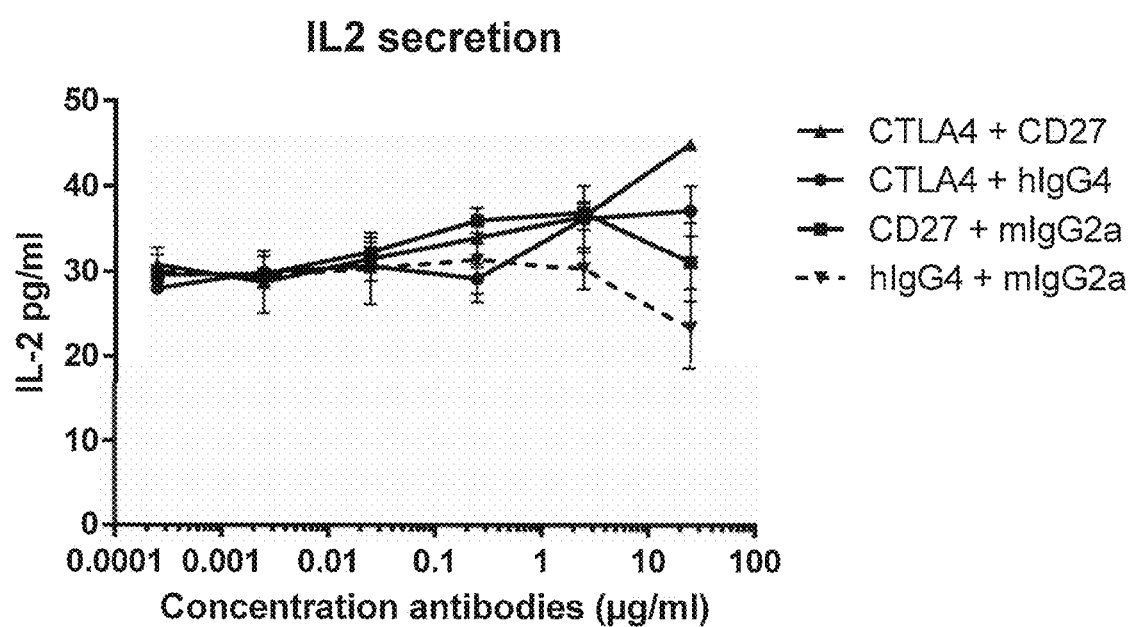
Figure 3A:
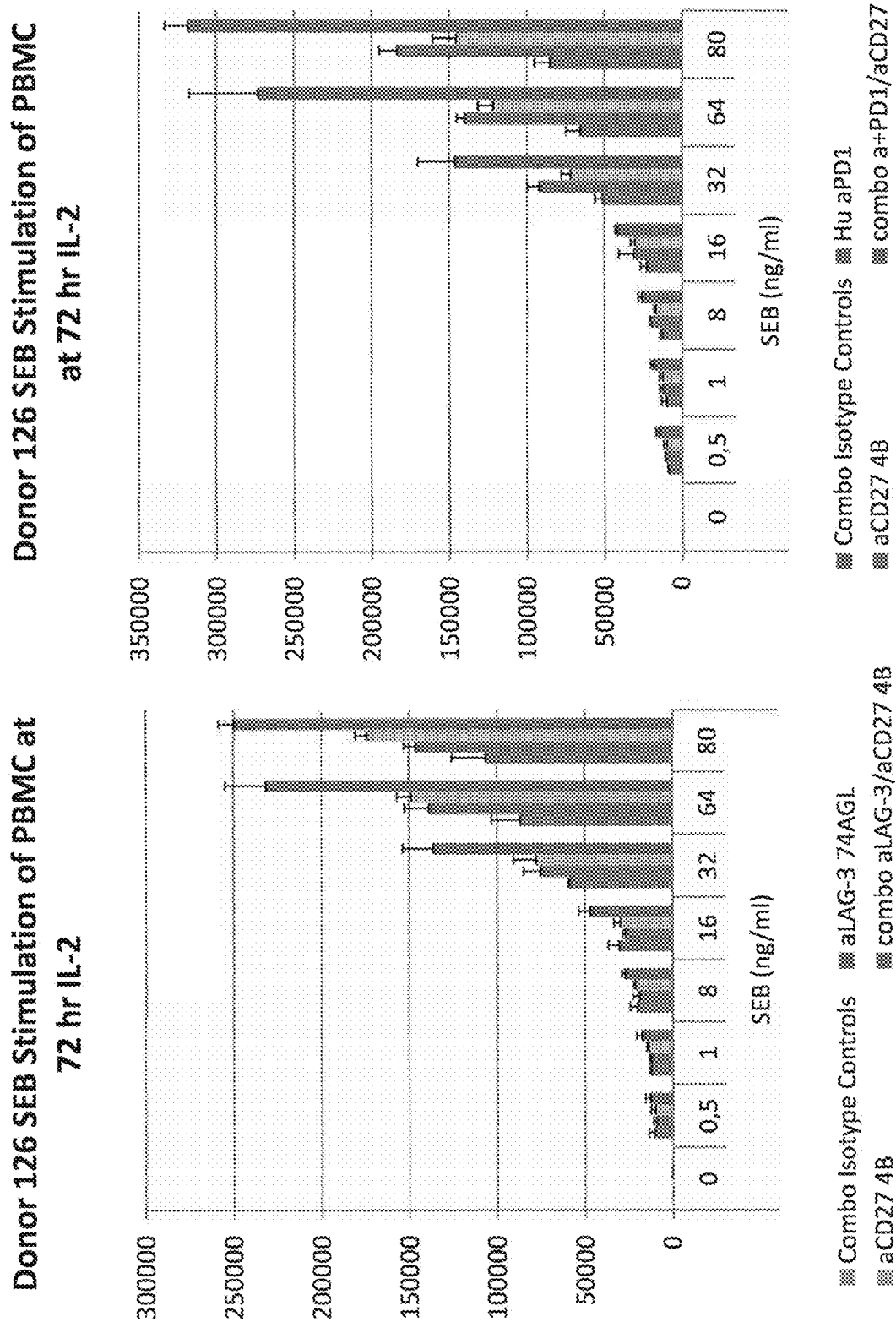
FIGS. 3A-D.
Figure 3B:
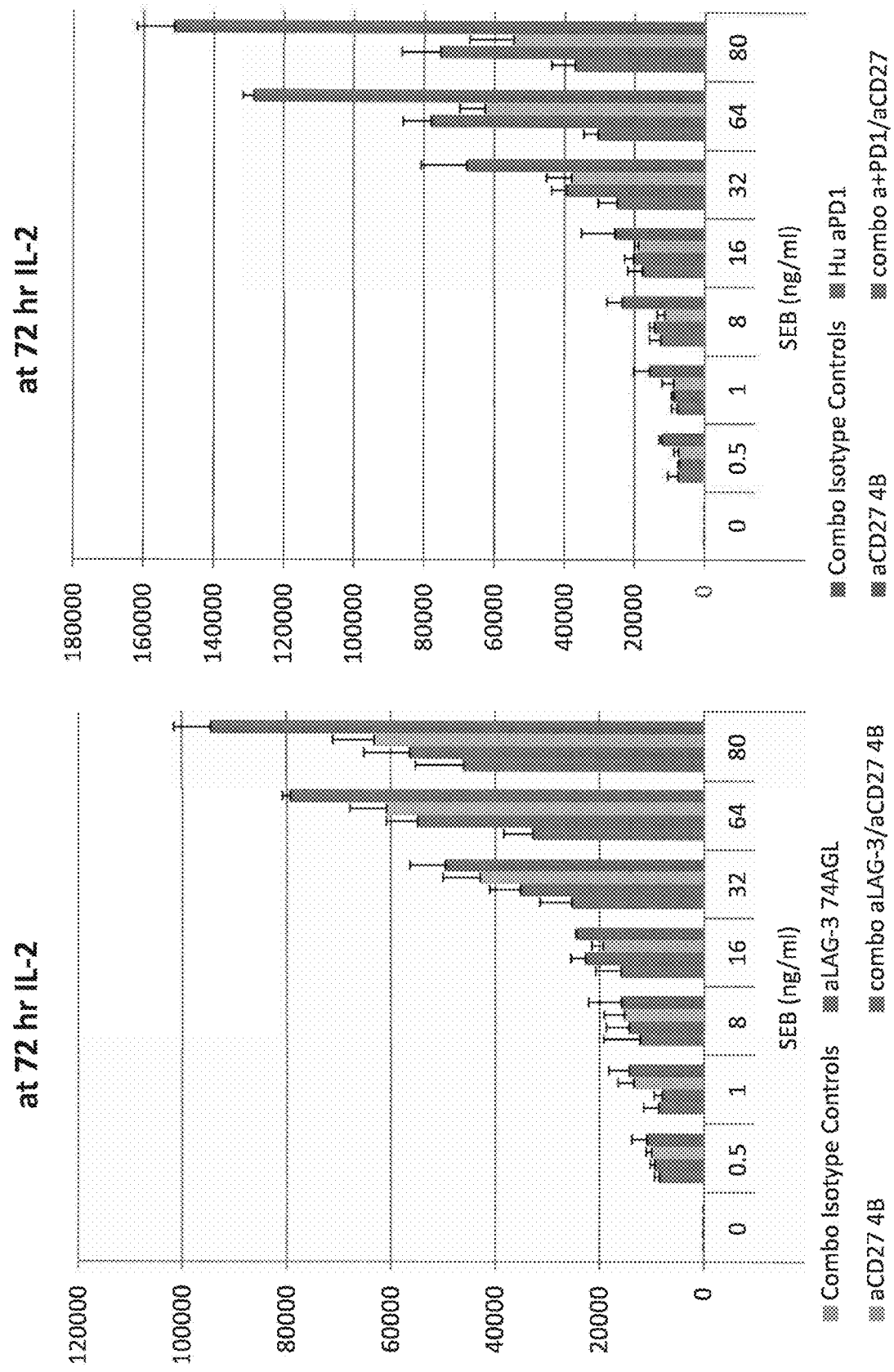
Figure 3C:
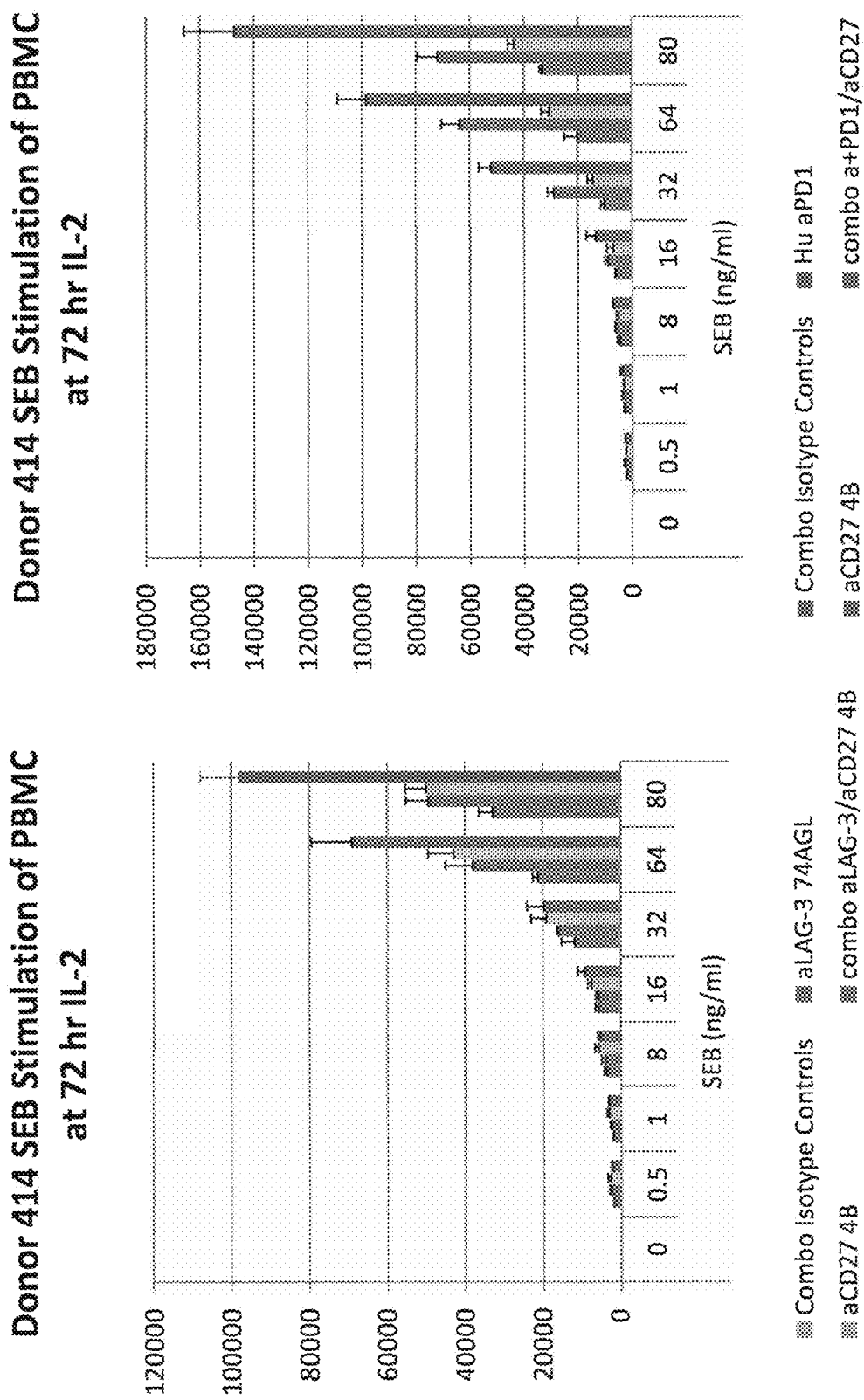
Figure 3D:
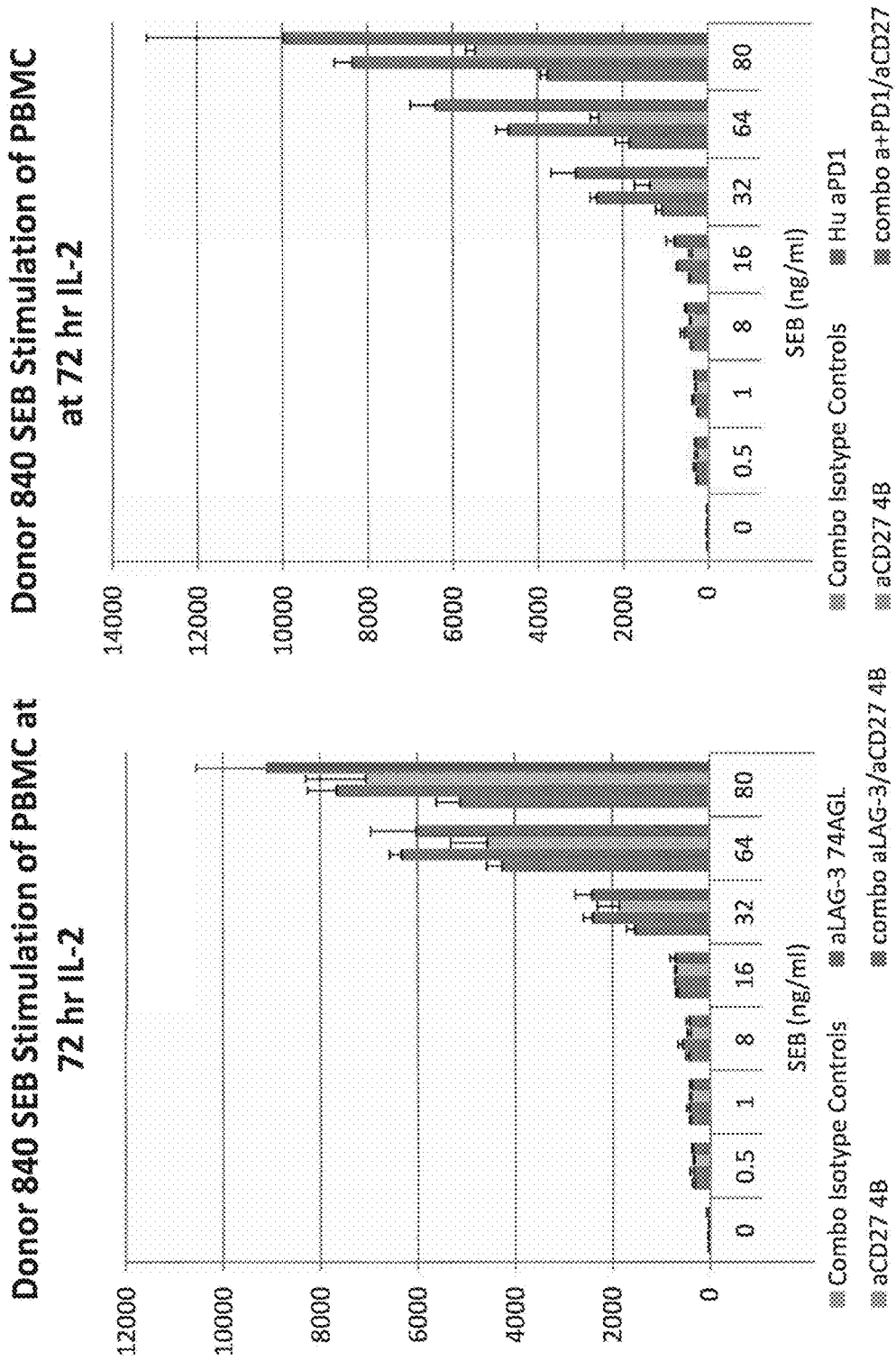

The expectation presented by these results, that combinations of a CD27 agonistic antibody with other immune check point inhibitors will give similar effects, was confirmed in additional experiments performed with the same whole blood test protocol, which included the combination of a CD27 agonist (hIgG4 chimera of hCD27.15, see above) with anti-CTLA4 (14D3, eBioscience 16.1529.82). The results of these experiments (see FIGS. 2A-2C) showed a similar cooperative action by the combination of the CD27 agonistic antibody and the CTLA4 inhibiting antibody in comparison to the individual antibodies alone (IgG4 isotype control as above; IgG2A isotype control: BD Pharmingen 554126).

On the basis of these results it may be expected that the combination of an anti-human CD27 agonistic antibody together with at least one immune checkpoint inhibitor will have beneficial effects in conditions ameliorated by stimulation of an immune response, such as conditions ameliorated by stimulation of antigen-specific T-lymphocytes.

Example 2

Evaluating the Activity of Anti-CD27, Anti-LAG-3, and Anti-PD1 Antibodies in a Human PBMC SEB Superantigen-Induced IL2 Secretion An additional confirmatory experiment was conducted to further show the effects of the combination of anti-human CD27 agonistic antibodies with immune checkpoint protein inhibitors. In this experiment a hCD27.15 analogue was used in combination with an anti-LAG3 antibody and an anti-PD1 antibody. The analogue used contains functional heavy chain CDR1, CDR2, CDR3 (SEQ ID NO: 1, 2, 3, respectively) and light chain CDR1, CDR2, CDR3 (SEQ ID NO: 4, 5, 6, respectively) of hCD27.15. In addition it contains functionally linked functional human IgG4 constant domains (CH1-CH3, GenBank accession #K01316). Functionality of the hCD27.15 analogue was established in a CD27 binding assay corresponding to the one disclosed in example 2 (page 49-50) of WO2012/004367 and a CD27 signaling test corresponding to the NF-κB tests disclosed in example 3 (page 54-55) of WO2012/004367.

The human anti-LAG3 antibody used comprised a heavy chain amino acid sequence according to SEQ ID NO: 23 and a light chain amino acid sequence according to SEQ ID NO: 24. The human anti-PD1 antibody used comprised a heavy chain amino acid sequence according to SEQ ID NO: 21 and a light chain amino acid sequence according to SEQ ID NO: 22. To study the effect of the combination of anti-human CD27 agonistic antibodies with immune checkpoint protein inhibitors human PBMCs were isolated from heparinized human blood from healthy donors using SepMate® tubes (Stem Cell). 15 ml of Ficoll-1077 was added to SepMate® tubes, which was carefully overlayed with 25 ml of human blood and centrifuged at 1,250 g for 12 min. at RT with light brake (5 out of 10—10 being max brake). White blood cells were isolated at the interphase of the Ficoll and dilute into 40 ml of Hanks Balances Salt Solution (HBSS) at RT. Next, cells were centrifuged at 300 g for 10 min. at 4° C. and the pellet was resuspended in 50 ml of HBSS. Finally, the cell suspension was centrifuged at 250 g for 10 min to remove platelets and the pellet was resuspended in 12 ml complete media (RPMI 1640 containing HEPES and Penn/Step and 10% human A+B+serum)). Cells were quantified by Vi-cell. Next, 50 µl of PBMC cell suspension ($1 \times 10^7$ cells/ml (final $5 \times 10^5$ cells/well) were plated in a 96-well round bottom plate. 50 µl of antibody (per antibody treatment, so 100 µl total antibody added for combination conditions) at 10 µg/ml end concentrations for 30 min. at 37° C. Next, a 4× concentration of 50 µl *Staphylococcus* enterotoxin B (SEB) superantigen (Toxin Technology, Sarasota, FL) at 0.5, 1, 8, 16, 32, 64 and 80 ng/ml end concentration was added and incubate 72 hr at 37° C. Supernatants were collected and cleared from any cell material by centrifugation. IL-2 secretion levels as a measure for immune activation was detected using Human IL-2 V-PLEX Kit (Catalog No. K151QQD-4, from Meso Scale Discovery, Rockville, MD), according to the manufacturer's instructions. As a negative control, (sub)-isotype matched antibodies were used.

FIGS. 3A-3D show the results obtained from four separate donors using the experimental methods described above. For each donor the results of the anti-CD27/Anti-LAG3 combination is shown in the left panel and the results of the anti-CD27/Anti-PD1 combination is shown in the right panel. For each SEB concentration the bars represent from left to right: isotype control; immune checkpoint inhibitor (anti-Lag3 or anti-PD1); anti-CD27; immune checkpoint inhibitor (anti-Lag3 or anti-PD1)+anti-CD27. The anti-CD27 antibody demonstrates approximately 1.5-2 fold IL-2 increase above isotype controls as a single agent. The anti-CD27 antibody showed combination activity with anti-LAG-3 antibody and with anti-PD1 antibody. Similar effects may be expected for combinations of anti-human CD27 agonistic antibody (including analogues) with other immune checkpoint protein inhibitors.

The invention is further described by the following numbered paragraphs:

1. An anti-human CD27 agonistic antibody, such as hCD27.15 or 1F5, or an antibody analogue thereof, for use in the treatment of a condition ameliorated by stimulation of an immune response, in particular stimulation of antigen-specific T-lymphocytes, wherein in said treatment a number of immune checkpoint protein inhibitors is administered.

2. An anti-human CD27 agonistic antibody according to paragraph 1, wherein an immune checkpoint protein inhibitor is selected from an inhibitor of CTLA-4, PD1, PD-L1, PD-L2, LAG-3, BTLA, B7H3, B7H4, TIM3 or KIR.

3. An anti-human CD27 agonistic antibody according to any of the paragraphs 1-2, wherein the condition ameliorated by immune stimulation, in particular stimulation of antigen-specific T-lymphocytes is selected from infectious diseases, such as bacterial, fungal, viral and parasitic infectious diseases, immunization against a pathogen, such as a pathogen selected from bacteria, fungi, viruses or parasites, or vaccination against toxins, or self-antigens, including antigens expressed on benign or malignant tumors, such as cancers, or conditions associated with uncontrolled proliferation of cells such as cancers.

4. An anti-human CD27 agonistic antibody according to any of the paragraphs 1-3, wherein the treatment is vaccination and a vaccine is administered in the treatment. 5. Immune checkpoint inhibitor for use in the treatment of a condition ameliorated by stimulation of an immune response, in particular stimulation of antigen-specific T-lymphocytes, wherein in said treatment an anti-human CD27 agonistic antibody, such as hCD27.15 or 1F5, or an antibody analogue thereof, is administered.

6. Immune checkpoint inhibitor according to paragraph 5, wherein the immune checkpoint inhibitor is selected from an inhibitor of CTLA-4, PD1, PD-L1, PD-L2, LAG-3, BTLA, B7H3, B7H4, TIM3 or KIR.

7. Immune checkpoint inhibitor according to any of the paragraphs 5-6, wherein the condition ameliorated by immune stimulation is selected from infectious diseases, such as bacterial, fungal, viral and parasitic infectious diseases, immunization against a pathogen, such as a pathogen selected from bacteria, fungi, viruses or parasites, or vaccination against toxins, or self-antigens, including antigens expressed on benign or malignant tumors, such as cancers, or conditions associated with uncontrolled proliferation of cells such as cancers.

8. An immune checkpoint inhibitor according to any of the paragraphs 5-7, wherein the treatment is vaccination and wherein a vaccine is administered in the treatment.

9. Combination of an anti-human CD27 agonistic antibody, such as hCD27.15 or 1F5, or an antibody analogue thereof, together with a number of immune checkpoint inhibitors for use in the treatment of a condition ameliorated by stimulation of an immune response, particularly stimulation of antigen-specific T-lymphocytes.

10. Combination according to paragraph 9, wherein an immune checkpoint inhibitor is selected from an inhibitor of CTLA-4, PD1, PD-L1, PD-L2, LAG-3, BTLA, B7H3, B7H4, TIM3 or KIR.

11. Combination according to any of the paragraphs 9-10, wherein the condition ameliorated by immune stimulation is selected from infectious diseases, such as bacterial, fungal, viral and parasitic infectious diseases, immunization against a pathogen, such as a pathogen selected from bacteria, fungi, viruses or parasites, or vaccination against toxins, or self-antigens, including antigens expressed on benign or malignant tumors, such as cancers, or conditions associated with uncontrolled proliferation of cells such as cancers.

12. Combination according to any of the paragraphs 9-11, wherein the treatment is vaccination and wherein a vaccine is administered in the treatment.

13. A method of treating a condition ameliorated by stimulation of an immune response, comprising administering to a subject in need thereof a therapeutically effective amount of an anti-human CD27 agonistic antibody and further an immune checkpoint protein inhibitor.

14. The method of paragraph 13, wherein said anti-human CD27 agonistic antibody is selected from the group consisting of: an anti-human CD27 agonistic antibody comprising the CDR amino acid sequences of SEQ ID NO: 1, 2, 3, 4, 5, 6, or a variant sequence; a humanized analogue of antibody hCD27.15; an analogue of antibody hCD27.15 that binds to the same epitope as hCD27.15; antibody 1F5; an anti-human CD27 agonistic antibody that does not require cross-linking.

15. The method of any of the paragraphs 13-14, wherein said further immune checkpoint inhibitor protein is selected from the group consisting of: an CTLA-4 antibody, an anti-PD1 antibody, an anti-PD-L1 antibody, an anti-PD-L2 antibody, an anti LAG-3 antibody, an anti-BTLA antibody, an anti-B7113 antibody, an anti-B7H4 antibody, an anti-TIM3 antibody and an anti-KIR antibody.

16. The method of any of the paragraphs 13-15, wherein said further immune checkpoint inhibitor protein is an anti-PD1 antibody.

17. The method of any of the paragraphs 13-16, wherein said anti-PD-1 antibody is pembrolizumab.

18. The method of any of the paragraphs 13-17, wherein said anti-PD-1 antibody is nivolumab.

19. The method of any of the paragraphs 13-18, wherein said further immune checkpoint inhibitor protein is an anti-LAG3 antibody.

20. The method of paragraph 19, wherein said anti-LAG3 antibody comprises the heavy chain and light chain amino acid sequences of SEQ ID NO: 23 and SEQ ID NO: 24, respectively.

21. The method of any of the paragraphs 13-20, wherein the subject in need of treatment suffers from cancer.

22. The method of any of the paragraphs 13-20, wherein the subject in need of treatment suffers from an infection (such as a bacterial, fungal, viral and parasitic infectious diseases).

23. A vaccine comprising an anti-human CD27 agonistic antibody and further comprising an immune checkpoint protein inhibitor.

24. The vaccine of paragraph 23, wherein said further immune checkpoint protein inhibitor is selected from the group consisting of: an CTLA-4 antibody, an anti-PD1 antibody, an anti-PD-L1 antibody, an anti-PD-L2 antibody, an anti LAG-3 antibody, an anti-BTLA antibody, an anti-B7H3 antibody, an anti-B7H4 antibody, an anti-TIM3 antibody and an anti-KIR antibody.

25. The vaccine of any of the paragraphs 23-24, wherein said further immune checkpoint inhibitor protein is an anti-PD1 antibody.

26. The vaccine of any of the paragraphs 23-25, wherein said anti-PD-1 antibody is pembrolizumab.

27. The vaccine of paragraphs 23-26, wherein said anti-PD-1 antibody is nivolumab.

28. The vaccine of any of the paragraphs 23-27, wherein said further immune checkpoint inhibitor protein is an anti-LAG3 antibody.

29. The vaccine of any of the paragraphs 23-28, wherein said anti-LAG3 antibody comprises the heavy chain and light chain amino acid sequences of SEQ ID NO:23 and SEQ ID NO:24, respectively.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating cancer, comprising administering to a subject in need thereof a therapeutically effective amount of an anti-human CD27 agonistic antibody and an immune checkpoint inhibitor which is an anti-LAG-3 antibody,
wherein said anti-human CD27 agonistic antibody is chosen from:
an anti-human CD27 agonistic antibody comprising:
a) a heavy chain comprising a heavy chain CDR1 comprising the sequence of SEQ ID NO: 1, a heavy chain CDR2 comprising the sequence of SEQ ID NO: 2, and a heavy chain CDR3 comprising the sequence of SEQ ID NO: 3, and
b) a light chain comprising a light chain CDR1 comprising the sequence of SEQ ID NO: 4, a light chain CDR2 comprising the sequence of SEQ ID NO: 5, and a light chain CDR3 comprising the sequence of SEQ ID NO: 6;
a humanized analogue of antibody hCD27.15; or antibody 1F5,
wherein said anti-LAG3 antibody comprises a heavy chain and a light chain comprising the amino acid sequences of SEQ ID NO: 23 and SEQ ID NO: 24, respectively,
wherein said anti-LAG-3 antibody is not a multispecific antibody that comprises additional immune checkpoint inhibitor components, and
wherein said method does not comprise administering to the subject a therapeutically effective amount of an anti-PD-L1 antibody or an additional immune checkpoint inhibitor.

2. The method of claim 1, wherein said anti-human CD27 agonistic antibody comprises:
a) the heavy chain comprising the heavy chain CDR1 comprising the sequence of SEQ ID NO: 1, the heavy chain CDR2 comprising the sequence of SEQ ID NO: 2, and the heavy chain CDR3 comprising the sequence of SEQ ID NO: 3, and
b) the light chain comprising a light chain CDR1 comprising the sequence of SEQ ID NO: 4, the light chain CDR2 comprising the sequence of SEQ ID NO: 5, and the light chain CDR3 comprising the sequence of SEQ ID NO: 6.

3. The method of claim 1, wherein said anti-human CD27 agonistic antibody comprises a heavy chain variable region comprising the sequence of SEQ ID NO: 8 and a light chain variable region sequence comprising the of SEQ ID NO: 10.

4. The method of claim 1, wherein said anti-human CD27 agonistic antibody comprises:
a) a heavy chain comprising a heavy chain CDR1 comprising the sequence of SEQ ID NO: 11, a heavy chain CDR2 comprising the sequence of SEQ ID NO: 12, and a heavy chain CDR3 comprising the sequence of SEQ ID NO: 13, and
b) a light chain comprising a light chain CDR1 comprising the sequence of SEQ ID NO: 14, a light chain CDR2 comprising the sequence of SEQ ID NO: 15, and a light chain CDR3 comprising the sequence of SEQ ID NO: 16.

5. The method of claim 1, wherein said anti-human CD27 agonistic antibody comprises a heavy chain variable region comprising the sequence of SEQ ID NO: 17 and a light chain variable region comprising the sequence of SEQ ID NO: 18.

* * * * *

SEQUENCE LISTING

<160> NUMBER OF SEQ ID NOS: 24

<210> SEQ ID NO 1
<211> LENGTH: 10
<212> TYPE: PRT
<213> ORGANISM: Mus musculus

<400> SEQUENCE: 1

Gly Phe Ile Ile Lys Ala Thr Tyr Met His
1               5                   10

<210> SEQ ID NO 2
<211> LENGTH: 17
<212> TYPE: PRT
<213> ORGANISM: Mus musculus

<400> SEQUENCE: 2

Arg Ile Asp Pro Ala Asn Gly Glu Thr Lys Tyr Asp Pro Lys Phe Gln
1               5                   10                  15

Val

<210> SEQ ID NO 3
<211> LENGTH: 7
<212> TYPE: PRT
<213> ORGANISM: Mus musculus

<400> SEQUENCE: 3

Tyr Ala Trp Tyr Phe Asp Val
1               5

<210> SEQ ID NO 4
<211> LENGTH: 11
<212> TYPE: PRT
<213> ORGANISM: Mus musculus

<400> SEQUENCE: 4

Arg Ala Ser Glu Asn Ile Tyr Ser Phe Leu Ala
1               5                   10

<210> SEQ ID NO 5
<211> LENGTH: 7
<212> TYPE: PRT
<213> ORGANISM: Mus musculus

<400> SEQUENCE: 5

His Ala Lys Thr Leu Ala Glu
1               5

<210> SEQ ID NO 6
<211> LENGTH: 10
<212> TYPE: PRT
<213> ORGANISM: Mus musculus

<400> SEQUENCE: 6

Gln His Tyr Tyr Gly Ser Pro Leu Thr Phe
1               5                   10

<210> SEQ ID NO 7
<211> LENGTH: 348
<212> TYPE: DNA
<213> ORGANISM: Mus musculus

<400> SEQUENCE: 7
gaggttcggc tgcagcagtc tggggcagac cttgtgaagc caggggcctc agtcaagttg      60

```
tcctgcacag cttctggctt catcattaaa gccacctata tgcactgggt gaggcagagg    120
cctgaacagg gcctggagtg gattggaagg attgatcctg cgaatggtga actaaatat    180 gacccgaagt tccaggtcaa ggccactata acagcagaca catcctccag cacagcctac    240
ctgcagctca acagcctgac atctgacgac actgccgtct attactgtgc tagatacgcc    300
tggtacttcg atgtctgggg cgcagggacc acggtcaccg tctcctca                348
```

<210> SEQ ID NO 8
<211> LENGTH: 116
<212> TYPE: PRT
<213> ORGANISM: Mus musculus

<400> SEQUENCE: 8

```
Glu Val Arg Leu Gln Gln Ser Gly Ala Asp Leu Val Lys Pro Gly Ala
1               5                   10                  15

Ser Val Lys Leu Ser Cys Thr Ala Ser Gly Phe Ile Ile Lys Ala Thr
            20                  25                  30

Tyr Met His Trp Val Arg Gln Arg Pro Glu Gln Gly Leu Glu Trp Ile
        35                  40                  45

Gly Arg Ile Asp Pro Ala Asn Gly Glu Thr Lys Tyr Asp Pro Lys Phe
    50                  55                  60

Gln Val Lys Ala Thr Ile Thr Ala Asp Thr Ser Ser Ser Thr Ala Tyr
65                  70                  75                  80

Leu Gln Leu Asn Ser Leu Thr Ser Asp Asp Thr Ala Val Tyr Tyr Cys
                85                  90                  95

Ala Arg Tyr Ala Trp Tyr Phe Asp Val Trp Gly Ala Gly Thr Thr Val
            100                 105                 110

Thr Val Ser Ser
        115
```

<210> SEQ ID NO 9
<211> LENGTH: 321
<212> TYPE: DNA
<213> ORGANISM: Mus musculus

<400> SEQUENCE: 9

```
gacatccaga tgactcagtc tccagcctcc ctgtctgcat ctgtgggaga cactgtcact    60
atcacatgtc gggcaagtga gaatatttac agttttttag catggtatca tcagaaacag    120
ggaaggtctc cgcaactcct ggtctatcat gcaaaaaccc tagcagaagg tgtgccatca    180
aggttcagtg gcagtggatc aggcacacag ttttctctga agatcaacag cctgcaggct    240
gaagattttg ggagttatta ctgtcaacat tattatggta gtccgctcac gttcggtgct    300
gggaccaagc tggaggtgaa a                                              321
```

<210> SEQ ID NO 10
<211> LENGTH: 107
<212> TYPE: PRT
<213> ORGANISM: Mus musculus

<400> SEQUENCE: 10

```
Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Tyr Ser Phe
            20                  25                  30

Leu Ala Trp Tyr His Gln Lys Gln Gly Arg Ser Pro Gln Leu Leu Val
        35                  40                  45
```

Tyr His Ala Lys Thr Leu Ala Glu Gly Val Pro Ser Arg Phe Ser Gly
            50                  55                  60

Ser Gly Ser Gly Thr Gln Phe Ser Leu Lys Ile Asn Ser Leu Gln Ala
65                  70                  75                  80

Glu Asp Phe Gly Ser Tyr Tyr Cys Gln His Tyr Tyr Gly Ser Pro Leu
                85                  90                  95

Thr Phe Gly Ala Gly Thr Lys Leu Glu Val Lys
            100                 105

<210> SEQ ID NO 11
<211> LENGTH: 10
<212> TYPE: PRT
<213> ORGANISM: Mus musculus

<400> SEQUENCE: 11

Gly Phe Thr Phe Ser Ser Tyr Asp Met His
1               5                   10

<210> SEQ ID NO 12
<211> LENGTH: 17
<212> TYPE: PRT
<213> ORGANISM: Mus musculus

<400> SEQUENCE: 12

Val Ile Trp Tyr Asp Gly Ser Asn Lys Tyr Tyr Ala Asp Ser Val Lys
1               5                   10                  15

Gly

<210> SEQ ID NO 13
<211> LENGTH: 10
<212> TYPE: PRT
<213> ORGANISM: Mus musculus

<400> SEQUENCE: 13

Gly Ser Gly Asn Trp Gly Phe Phe Asp Tyr
1               5                   10

<210> SEQ ID NO 14
<211> LENGTH: 11
<212> TYPE: PRT
<213> ORGANISM: Mus musculus

<400> SEQUENCE: 14

Arg Ala Ser Gln Gly Ile Ser Arg Trp Leu Ala
1               5                   10

<210> SEQ ID NO 15
<211> LENGTH: 7
<212> TYPE: PRT
<213> ORGANISM: Mus musculus

<400> SEQUENCE: 15

Ala Ala Ser Ser Leu Gln Ser
1               5

<210> SEQ ID NO 16
<211> LENGTH: 10
<212> TYPE: PRT
<213> ORGANISM: Mus musculus

<400> SEQUENCE: 16

Gln Gln Tyr Asn Thr Tyr Pro Arg Thr Phe

-continued

<210> SEQ ID NO 17
<211> LENGTH: 119
<212> TYPE: PRT
<213> ORGANISM: Mus musculus

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Asn Trp Gly Phe Phe Asp Tyr Trp Gly Gln Gly
            100                 105                 110

Thr Leu Val Thr Val Ser Ser
        115

<210> SEQ ID NO 18
<211> LENGTH: 107
<212> TYPE: PRT
<213> ORGANISM: Mus musculus

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Arg
                85                  90                  95

Thr Phe Gly Gln Gly Thr Lys Val Glu Ile Lys
            100                 105

<210> SEQ ID NO 19
<211> LENGTH: 447
<212> TYPE: PRT
<213> ORGANISM: Artificial Sequence
<220> FEATURE:
<223> OTHER INFORMATION: Description of Artificial Sequence: Synthetic
      humanized polypeptide

<400> SEQUENCE: 19

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

```
Tyr Met Tyr Trp Val Arg Gln Ala Pro Gly Gln Gly Leu Glu Trp Met
        35                  40                  45

Gly Gly Ile Asn Pro Ser Asn Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

-continued

```
<210> SEQ ID NO 20
<211> LENGTH: 218
<212> TYPE: PRT
<213> ORGANISM: Artificial Sequence
<220> FEATURE:
<223> OTHER INFORMATION: Description of Artificial Sequence: Synthetic
      humanized polypeptide

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 440
<212> TYPE: PRT
<213> ORGANISM: Homo sapiens

<400> SEQUENCE: 21

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95
```

```
Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 22
<211> LENGTH: 214
<212> TYPE: PRT
<213> ORGANISM: Homo sapiens

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 23
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
            35                  40                  45

Gly Glu Ile Asn His Arg Gly Ser Thr Asn Ser Asn Pro Ser Leu Lys
 50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val

```
                    165                 170                 175
Leu Gln Ser Ser Gly Leu Tyr Ser Leu Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 24
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

-continued

```
Glu Asp Phe Ala Val Tyr Tyr Cys Gln Gln Arg Ser Asn Trp Pro Leu
                85              90                  95

Thr Phe Gly Gln Gly Thr Asn Leu Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
            130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys
210
```